United States Patent
Loughney et al.

(10) Patent No.: US 10,602,973 B2
(45) Date of Patent: Mar. 31, 2020

(54) NON-INVASIVE DETECTION OF THE BACKFLOW OF URINE

(71) Applicant: National University of Ireland, Galway, Galway, County Galway (IE)

(72) Inventors: Sarah Loughney, Dublin (IE); Mark Bruzzi, Galway (IE); Martin O'Halloran, Galway (IE); Prem Puri, Dublin (IE); Ricardo Eleuterio, Evora (PT)

(73) Assignee: National University of Ireland, Galway, Galway (IE)

( * ) Notice: Subject to any disclaimer, the term of this patent is extended or adjusted under 35 U.S.C. 154(b) by 207 days.

(21) Appl. No.: 15/571,225

(22) PCT Filed: May 6, 2016

(86) PCT No.: PCT/EP2016/060234
§ 371 (c)(1),
(2) Date: Nov. 1, 2017

(87) PCT Pub. No.: WO2016/177901
PCT Pub. Date: Nov. 10, 2016

(65) Prior Publication Data
US 2018/0263546 A1 Sep. 20, 2018

Related U.S. Application Data

(60) Provisional application No. 62/157,752, filed on May 6, 2015.

(51) Int. Cl.
*A61B 5/05* (2006.01)
*A61B 5/20* (2006.01)
(Continued)

(52) U.S. Cl.
CPC .............. *A61B 5/201* (2013.01); *A61B 5/053* (2013.01); *A61B 5/0531* (2013.01);
(Continued)

(58) Field of Classification Search
CPC .. A61B 5/20; A61B 5/00; A61B 5/053; A61B 5/7203; A61B 5/201; A61B 5/204;
(Continued)

(56) References Cited

U.S. PATENT DOCUMENTS

| | | | | |
|---|---|---|---|---|
| 2004/0019292 A1* | 1/2004 | Drinan | ................. | G06K 9/0002 600/547 |
| 2004/0030258 A1* | 2/2004 | Williams | ............. | A61B 5/0478 600/544 |
| 2016/0029953 A1* | 2/2016 | Bonomi | ............... | A61B 5/0537 600/529 |

FOREIGN PATENT DOCUMENTS

| | | |
|---|---|---|
| AU | 2011 202 767 | 6/2011 |
| GB | 2504299 | 1/2014 |

OTHER PUBLICATIONS

International Search Report and Written Opinion dated Jul. 18, 2016 corresponding to International Patent Application No. PCT/EP2016/060234.
(Continued)

*Primary Examiner* — Eric J Messersmith
(74) *Attorney, Agent, or Firm* — Leason Ellis LLP

(57) ABSTRACT

The present relates to a method, system and a device for non-invasive detection of urine flow from the bladder into the kidney(s). The method, system and device rely on measurements made at distinct time points and can be used to detect Vesicoureteral reflux. The method, system and device are designed to detect changes in urine volume in the ureter(s), bladder and/or kidney(s). The method and device
(Continued)

(a)

(b)

measure conductivity changes by bioelectrical impedance or electrical impedance tomography technology.

12 Claims, 18 Drawing Sheets

(51) Int. Cl.
*A61B 5/00* (2006.01)
*A61B 5/053* (2006.01)
*A61B 5/11* (2006.01)
*A61B 5/01* (2006.01)

(52) U.S. Cl.
CPC ............ *A61B 5/0536* (2013.01); *A61B 5/204* (2013.01); *A61B 5/208* (2013.01); *A61B 5/6808* (2013.01); *A61B 5/7203* (2013.01); *A61B 5/742* (2013.01); *A61B 5/01* (2013.01); *A61B 5/11* (2013.01); *A61B 5/207* (2013.01); *A61B 5/6823* (2013.01); *A61B 5/6831* (2013.01); *A61B 5/6833* (2013.01); *A61B 2503/04* (2013.01); *A61B 2503/06* (2013.01); *A61B 2560/0214* (2013.01); *A61B 2560/0468* (2013.01)

(58) Field of Classification Search
CPC ..... A61B 5/208; A61B 5/6808; A61B 5/0531; A61B 5/742; A61B 5/0536; A61B 5/6831; A61B 2560/0214; A61B 5/01; A61B 5/11; A61B 5/207; A61B 5/6823; A61B 2560/0468; A61B 2503/06; A61B 2503/04; A61B 5/6833
See application file for complete search history.

(56) References Cited

OTHER PUBLICATIONS

Bayram: "Poster Session Behavior disorders and quality of life in children and adolescents with renal transplantation", Pediatric Nephrology.,vol. 26, No. 9, Jul. 13, 2011 (Jul. 13, 2011), pp. 1591-173.
Anonymous: "Clinical Practice: Quadscan 4000 & Touch Screen", Bodystat, Jan. 1, 2014 (Jan. 1, 2014), pp. 1-16, Retrieved from the Internet: URL:http://www.bodystat.com/pdf/spreads/quadscan.pdf [retrieved on Jun. 20, 2016].
Anonymous: "Quadscan4000 Touch Screen Specifications", Bodystat, Retrieved from the Internet: URL:http://www.bodystat.com/products/quadscan [retrieved on Jun. 20, 2016].
Meral Torun Bayram et al: "Bioelectric Impedance Analysis in the Diagnosis of Vesicoureteral Reflux", Iranian Journal of Pediatrics, vol. 25, No. 4, Aug. 24, 2015 (Aug. 24, 2015).

* cited by examiner (a)    (b)

(b)

(a)

NON-INVASIVE DETECTION OF THE BACKFLOW OF URINE

FIELD OF THE INVENTION

The present relates to a system, method and a device for non-invasive detection of urine flow from the bladder into the kidney(s). The system, method and device rely on measurements made at distinct time points and can be used to detect Vesicoureteral Reflux (VUR). The system, method and device are designed to detect changes in urine volume in the ureter(s), bladder and/or kidney(s). The system, method and device measure conductivity changes by bio-electrical impedance or Electrical Impedance Tomography (EIT) technology.

BACKGROUND OF THE INVENTION

VUR is a condition that mostly occurs in young children and involves backflow of urine from the bladder through the ureters into the kidneys and may lead to life-threatening damage to the kidneys. VUR may involve a single or double urinary collecting system i.e. a single ureter (unilateral) or both ureters (bilateral). The need for a non-invasive method of detecting Vesicoureteral Reflux (VUR) in children is clear based on the levels of anxiety observed in patients, parents and practitioners during a Voiding Cystourethrogram (VCUG) procedure, which is the current gold standard for diagnosing VUR. In this context detection includes the initial diagnosis of the condition as well as monitoring a patient that has already been diagnosed to determine if the condition has resolved or progressed as well as monitoring a patient following surgery to determine if the condition has resolved or progressed.

Primary VUR mostly occurs in young children (<5 years). It is estimated to be prevalent in 1-2% of the paediatric population and in 30% to 40% of children presenting with a Urinary Tract Infections (UTIs). VUR is a risk factor for renal parenchymal damage (RPD) or renal scarring. In the case of extensive scarring, renal injury may result in hypertension, decreased renal function, proteinuria and in certain cases End Stage Renal Disease (ESRD). In a prospective, population-based registry of children in Italy with Chronic Renal Failure (CRF), VUR was the leading single cause of CRF accounting for 25.4% of all patients with CRF.

Cohorts of patients who will benefit from the present invention includes patients presenting with UTIs (in particular those under 5 years), children with hydronephrosis and siblings and children of those with VUR.

Currently, when a child is referred to a radiologist with suspected VUR, they may be evaluated using Renal Bladder Ultrasound (RBUS), Voiding Cystourethrogram (VCUG), Nuclear Cystogram and or Dimercaptosuccinic Acid (DMSA). Each of these methods, currently used to assess patients with suspected VUR have at least one major drawback associated with it:
  VCUG is the gold standard for grading VUR, however it involves both catheterisation and significant radiation exposure. During a VCUG a catheter is placed in the patient's urethra and a radiopaque contrast is instilled through the catheter into the bladder. The kidney(s), ureter(s) and bladder are observed as the bladder is filled and fluoroscopy is used to image the patient during urination to detect VUR.
  RBUS it is not considered to be a reliable indicator of VUR (approximately 26% accurate).
  DMSA is an expensive test, involves significant radiation exposure and must be carried out by nuclear medicine specialist. DMSA may not detect VUR, but is used to indicate if there is already damage in the kidneys.
  Nuclear Cystograms also require catheter passage and radiation exposure to accurately detect VUR. Radionuclide is instilled into the bladder and the patient is imaged using a gamma camera. Radiation exposure is reduced, however image quality may be poor.

If VUR is diagnosed or treated, repeat tests are required at regular intervals to determine if reflux has resolved or progressed. Repeat VCUG tests are often avoided based on levels of anxiety experienced by child, parent and treating physician during initial VCUG evaluations. Changes in volume of urine in the kidney at defined time points, namely as bladder pressure increases during micturition or filling, or as bladder pressure increases as pressure is applied to the abdomen and hence to the bladder, either manually or by the system itself, are indications for Vesicoureteral Reflux (VUR). If a patient suffers from VUR the impedance within the kidney(s) and or ureter(s) will increase during urination, if no VUR is present there may be little or no change observed in the kidney(s) and or ureter(s).

Bioelectrical impedance measurement involves using a pair of skin contacting electrodes to feed an electrical current into the body and measuring the resulting voltages between the same or a second electrode pair at the surface of the body adjacent to the kidney(s) or ureter(s). An apparatus for measuring bioelectrical impedance is known from the U.S. Pat. No. 6,339,722B1. This bioelectrical impedance measurement system is used to determine biological parameters concerning a bodily fluid.

Electrical Impedance Tomography (EIT) provides an impedance distribution image based on changes in impedance across a plane, where the impedance distribution image is defined by the position of the electrodes. The principle for using an EIT system to display impedance distribution images relating to parts of the human body is described in US patent 20030216664A1.

The prior art describes the concept of analysing retroperitoneal bleeding, bladder conditions, bladder function and bladder volumes and gastro-oesophageal reflux using Bioelectrical Impedance. However, no document describes use of bioelectrical impedance as a non-invasive means of measuring kidney function or reflux of urine into the kidney.

Studies have assessed impedance changes in the bladder, to provide signals to patients to indicate changes in bladder volume for patients suffering from paraplegia, or patients with other conditions that show an impaired perception of bladder filling level, that may result in incontinence or damage to the urogenital system. Studies have shown a dynamic change in impedance during bladder filling and following bladder voiding using bioelectrical impedance. For example prior art that describes a device for monitoring bladder urine volume based on bioelectrical impedance includes that described in U.S. Pat. No. 5,103,835 and CN104605850 which describes a method for monitoring bladder urine volume based on EIT. EIT has also been used for monitoring haemorrhaging from the kidneys (retroperitoneal bleeding). Studies evaluate if impedance changes in the space around the kidneys can be used to provide information to healthcare workers that internal bleeding is present. This is a useful indication for monitoring patients diagnosed with a blunt kidney trauma or following surgery on the kidneys.

The prior art also describes the concept of using bioelectrical impedance and more specifically EIT to monitor gastro-oesophageal reflux (GOR). GOR occurs when gastric contents flow from the stomach towards the oesophagus. EIT has been suggested as a possible means for removing the need for patient intubation to detect GOR. However in studies which investigate the feasibility of using EIT as an alternative method for identifying GOR, it has been concluded that it is not yet possible to detect GOR using EIT accurately. The study suggests that this may be based on the deep position of the oesophagus in the body, changes observed in the oesophagus during episodes of no reflux and the impedance range of the refluxed fluid and oesophagus contents.

Based on the impedance range of the different fluids of interest, the duration and timing of the events, impact of external organs, pathophysiology of conditions, patient cohorts and organ dimensions, it would not be obvious to the skilled person that use of EIT would be suitable or effective for detection of VUR.

The Conductivity of Different Fluids:

Different biological tissues and fluids have different conductivities, where the greater the difference in conductivity between the region of interest and surrounding regions, the easier it is to detect impedance changes. For example when detecting VUR the conductivity of urine and the kidney (at a frequency of 100 kHz) are approximately 2.3 S/m and 0.17 S/m respectively, a difference of 2.13 S/m. Where, the difference between Bladder and Urine is 2.09 S/m and Kidney and Blood is 0.53 S/m. No estimate of conductivity change values during GOR could be estimated this is due to conductivity the conductivity of gastric content varies considerably, depending on what food is consumed. As a result, the impedance difference between urine and the kidney is easier to detect and in addition it may be possible to further increase the conductivity difference by using an oral solution that further increases the impedance of urine (e.g. solution with high salt or ion concentration).

Duration and Timing:

EIT systems are most suitable for detecting dynamic changes—that occur suddenly at a known period of time. Bladder filling, kidney haemorrhage and GOR are often random, and occur over prolonged, unpredictable period of time. This limits EIT's utility for these applications. In contrast, VUR occurs when surges of highly conductive fluid (urine) travel from the bladder to the ureter(s) or kidney(s) when the bladder pressure increases (e.g. urination—an event that is predictable and rapid). The simultaneous occurrence of VUR and a high pressure event provides a known period of time when a child urinates and this data may be used to feedback into the system to define the period of time of interest and the reference timeframe to gather bioelectrical impedance measurements at a base line (when no urination occurs) and during urination to detect VUR. Impact of external organs—Bioelectrical impedance measurements are influenced by external factors, including the activity of organs surrounding the region of interest. Based on this, measurements will be impacted depending on the location of the body being monitored and different data analysis methods must be used to account for activity of surrounding organs. For example, activity of organs that are in close proximity to the oesophagus need to be considered when monitoring for gastroesophageal reflux (GOR). These may include breathing (air in the lungs), the heart beating and digestion of stomach contents. In contrast the physiological parameters that may impact Vesicoureteral Reflux may include intestinal movement, breathing and volume of urine in the bladder.

The Pathophysiology of the Conditions and Patient Cohort:

Primary VUR is generally caused by a shorter than normal intramural tunnel between the bladder and the ureter and is found in children between six months and five years of age and will often resolve as the child grows. VUR is often diagnosed when the patient presents with recurrent or febrile urinary tract infections. Gastroesophageal reflux can be found in both adults and children and is often due to obesity, diet, and smoking or in certain cases a hernia. Gastroesophageal reflux is often encountered in conjunction with other gastric symptoms. Aside from urinary tract infections that are a risk factor for primary VUR. VUR is asymptomatic: the patient cannot feel when the condition occurs, whereas patients suffering from gastroesophageal reflux have distinct symptoms such as heartburn.

The Organ that Reflux Originates in and the Location where it is Measured are Different:

VUR occurs when urine travels from the bladder through the ureter towards the kidneys, however GOR occurs when gastric contents flows from the stomach towards the oesophagus. The kidney is a separate organ to the bladder, however the oesophagus is directly attached to the stomach. Gastroesophageal reflux is monitored in the oesophagus, and VUR is monitored in the kidneys after it has travelled through the ureters and thus has travelled through other space into a different organ before it is monitored. EIT results will also depend on the distance of the electrodes from the area of interest. The oesophagus is located closest to the front of the chest and the kidneys are located close to the back, just under the ribs. The electrode material and size must be selected and placed in a position to optimise the readings for each condition depending on the location of the organ.

Other groups have looked at non-invasive means for detecting VUR. WO2000027286 discloses a passive acoustic method of detecting the presence or absence of VUR in a patient, which comprises amplifying sounds from the abdomen of the patient from a time just prior to the onset of urination, and then detecting the presence or absence of an audio signal characteristic of VUR in the amplified sound. A clinical study using this method failed to interpret a signal in 11% of cases. US20100222699 discloses a non-invasive thermotherapy which heats bodily tissues and fluid (the urine in the bladder) using emitted energy and non-invasively measures the resulting temperature changes in the target and surrounding fluid and tissue (the kidneys) to detect and/or treat various physical conditions such as Vesicoureteral reflux. Safety concerns may be attributed to using microwave energy to heat internal organs in children.

OBJECT OF THE INVENTION

The object of the present invention is to provide a device, system and method to determine functional kidney characteristics, which are indicative of changes in volume of urine in the ureters, bladder and/or kidney(s), which may be used to detect VUR and if that VUR is likely to be clinically significant and if the patient requires further evaluation.

A further object is to provide a device that is relatively inexpensive, portable and non-invasive. In other words it will not involve use of radiation exposure or catheterisation. A still further object is to provide a system, device and a method, which will minimise the anxiety experienced by children, parents and health care workers in diagnosing VUR thereby improving compliance with clinical guidelines. It is a particular object to provide a device, system and method that can be used at the point of care in the emergency department of the hospital, the physician's office or clinic in order to simplify patient care. It is also an object to use the system to follow-up with patients previously diagnosed to determine if their original condition has improved or deteriorated. In addition it is an object to provide a system, device and method, which may allow patients to undergo continuous monitoring in a convenient and comfortable location. In certain situations there is also a need to improve the accurate detection of clinically significant VUR, and this can be achieved by the present invention by gathering data over a number of urination cycles in order to provide a more accurate reflection of the condition. The system and method should display the functional kidney characteristics in a manner, which is easily perceived and interpreted by the user.

SUMMARY OF THE INVENTION

Accordingly the invention provides a system for measuring urine flowing from the bladder to the kidney(s) or ureter(s) in a subject using bioelectrical impedance technology or Electrical Impedance Tomography (EIT), the system comprising an impedance measurement module configured to record impedance measurements in the kidney(s) or ureter(s), and a processor configured to receive data from the impedance measurement module, the data being impedance measurements taken over a period of time, and the processor being further configured to analyse the differences between measurements or groups of measurements to provide an indication of volume changes in the kidney.

In other words the system measures the presence or volume of urine in the kidney.

The impedance measurement module may comprise a plurality of electrodes adapted to record impedance measurements, the electrodes being adapted to be placed in conductive contact or to be capacitively coupled with the skin and being connectable to a control unit.

The impedance measurement module may comprise at least two electrodes. The electrodes may be incorporated into a wearable unit. The control unit may be also be incorporated into the wearable unit.

The processor may be configured to produces graphs or images to provide an indication of urine volume changes in the kidney over a period of time.

Measurements may be taken as bladder pressure increases during micturition or filling, or as bladder pressure increases as pressure is applied to the abdomen and hence to the bladder, either manually or by the system itself. Data may be collected during micturition and compared to a baseline measurement taken when no micturition is occurring.

The system may comprise means for securing the wearable unit to the body selected from a quick release fastener, an elastic strap, a harness securable around the thighs and/or shoulders or neck, a bib, brace, sling or halter.

The invention also provides a method for detecting urine flowing from the bladder to the kidney(s) or ureter(s) in a subject comprising recording conductivity changes occurring in the ureters, bladder and/or kidneys which indicate changes in volume in the ureters, bladder and/or kidney wherein conductivity changes are detected by bioelectrical impedance or electrical impedance tomography and these volumes being compared to control values to indicate the presence or absence of VUR in the test subject.

In a further aspect the invention provides a device for detecting urine flowing from the bladder to the kidney(s) in a subject using bioelectrical impedance technology or electrical impedance tomography, wherein said device comprises an impedance measurement module configured to record impedance measurements in the kidney(s) or ureter(s), and a processor configured to receive data from the impedance measurement module, the data being impedance measurements taken over a period of time, and the processor being further configured to analyse the differences between the measurements or groups of measurements, to provide an indication of volume changes in the ureter(s) and/or kidney(s) over a period of time.

The invention involves a system, method and device to detect urine flow from the bladder in the direction towards the kidney(s) in humans and animals, by recording impedance changes occurring in the ureters, bladder or kidney(s) that will indicate changes in volume of urine in the ureters, bladder or kidney(s). The volume of urine travelling to the kidneys may be measured during periods when bladder pressure increases either naturally (during urination or bladder filling) or when induced by manually pressing on the bladder or by measuring the residual volume of urine left in the bladder following urination.

Accordingly the invention provides a method, device and system for measuring and detecting urine flow from the bladder to the kidney(s) using bioelectrical impedance, wherein said system/device comprises an impedance measurement module that comprises at least two electrodes and a control unit that measure impedance changes over a time period. The system/device also comprises a processor that receives the impedance measurements and analyses the output to estimate impedance changes over the time period. The analysis may output graphs to display the average change in impedance over time. A graph may be analysed at a base-line (when no urination is occurring) and during urination to determine if changes in the graph can be observed between baseline measurement and measurements during urination or the changes are increasing over time during urination. A change in impedance can be correlated to VUR.

To further analyse the bioelectrical impedance output the system/device may use electrical impedance tomography technology. The impedance measurement module may comprise a plurality of electrodes which may be placed around the plane of the body at the level of the kidneys, and a control unit to inject current and to measure impedance changes over a time period. The processor receives the impedance measurements and analyses the output to estimate changes in impedance distribution images over the time period.

The impedance measurement module of the system/device may comprise a plurality of electrodes incorporated into a wearable unit and an electronic control unit, the electrodes being spaced around the circumference of the unit, the control unit being connectable to the wearable unit and the control unit connectable to a processor that may be configured to receive and analyse the impedance measurements over a period of time. The processor may be integrated into or connectable with a display unit that communicates to the user if there are changes in urine volume in the ureter(s), bladder and/or kidney(s).

The wearable unit may comprise a belt or a patch.

The electrodes may be spaced approximately evenly around the full circumference of the belt. Alternatively, the plurality of electrodes may be spaced evenly around a partial circumference of the belt to form a hemi-array. The patch may be stuck to the patient, the patch containing electrodes.

The electrodes may function in pairs during both current injection and voltage measurement. The current is applied between electrode pairs and the voltages measured between electrode pairs.

The belt may be formed in two layers in which the outer layer material of the electrode belt is preferably water resistant to protect against ingress of water into electronic components. The inner layer may comprise electrodes and/or incorporate adhesive and/or discrete sections of high friction material (e.g. silicone or vinyl) to prevent movement. The material is preferably selected to be biocompatible.

The electrodes will not be touching each other and may comprise discrete portions of conductive material (with approximate average surface resistivity of 8-105 ohm/sq) in contact with the skin. The electrodes may be in direct conductive contact or capacitively coupled to the body surface. The electrodes may be in contact with a non-conductive material (e.g. gel layer) that is in contact with the skin. Ultrasound imaging or x-ray may be used to identify the exact location of the ureter(s); bladder and/or kidney(s) to make sure that the electrodes or belt or patch are correctly positioned.

The electrode belt or patch may comprise active electrodes, where each electrode contains an active electronic chip.

An active electrode in the context of this invention may use the same configuration as Gaggero et al, containing a chip with embedded voltage buffers, switches and a microprocessor. The active electrode produces an exciting effect that is used to stimulate and measure potentials from a localized area. It may also be known as an exciting electrode, a localizing electrode, or a therapeutic electrode. In use the electronic chips may contain electrodes. The active electronic chips may be connected to each other through a connection such as a flexible printed cable, flat cable or bus lines and may be connected to the control unit similarly. Alternatively the chips may be integrated into the control unit and connected to the electrodes via bus lines e.g. flexible, flat or printed cables.

The belt may further comprise a means for securing it at the front of the torso of a patient. Such a means may be a quick release fastener for safety or an elastic strap to allow adjustment to body shape or size and for securing the belt on a patient. Alternatively the belt may comprise a harness securable around the thighs and/or shoulders and/or neck for securing the belt and control unit on a patient. In such an embodiment the control unit may attach and detach directly to and from the harness. In alternative embodiments the device may comprise a bib, brace, sling or halter to support the belt and control unit on the patient. In a still further embodiment the control unit and electrodes may attach directly to a diaper or shorts comprising absorbable (nappy or diaper-type) material. The belt may be wider at the back and narrower at the front to ensure unrestricted breathing by the patient.

To detect VUR the device/system may measure impedance changes during micturition and before or after micturition (to obtain a base-line measurement). For a patient that has VUR, during micturition the volume of urine refluxed may be proportional to the volume of urine passed. During urination a predefined volume of urine may be needed to detect VUR. The device/system may comprise urination sensors (e.g. a wetness indicator, and/or a humidity or temperature sensor). The function of urination sensors (e.g. wetness indicator and humidity or temperature sensor) is to signal to a person when a pre-defined volume of urine has been passed and provide a time point and signal for when micturition has started and ended and when data will be received and analysed. This is particularly important for young children and babies that may not be toilet trained, in these patients micturition is unpredictable and occasionally the volume of urine passed is very small. As a result the system may need to record and continuously gather data for up to four hours to catch a reflux event where a sufficient volume of urine is passed. Gathering data over a longer period of time requires that the control unit contains greater battery power and higher data storage capacity. This may translate into a larger and heavier battery and storage medium and hence a larger control unit. Some advantages of incorporating a sensor (e.g. wetness indicator and humidity or temperature) include that the system remains as light and compact as possible so that it is portable and comfortable for the child to wear, less data analysis is required, reducing signal processing time—if hours of data are presented the user or processor does not know when micturition occurred and may need to analyse a large volume of data. The signals from the sensors may be input into a feedback loop and used to activate the control unit to begin measuring when micturition begins and to stop measuring after it is finished. This allows the device/system to only measure impedance changes during micturition and baseline and results in a lighter, more compact control unit and more efficient processing of data. The sensors may also be used to emit a signal when a significant volume of urine has passed and/or when urination starts or finishes. The signal may be a noise or light or colour change displayed on the control unit or display unit.

If the user is aware that sufficient volume of urine has passed they will not need to remove the device, where removing the device prematurely, may disturb the electrode position and impact the accuracy of the results.

Both adult and baby nappies and diapers have incorporated wetness indicators for some time. Generally, wetness indicators display a colour change when in contact with a significant amount of liquid. However, for the device/system of the invention such an indicator would correlate to a specific amount of liquid that would indicate that a reflux event (if it has occurred) may be detected. This may be achieved by applying a wetness indicator to a hot melt adhesive on the inside of a backsheet material in contact with an absorbent core of known absorbency activating the indicator when a specific volume of fluid is present.

Humidity and temperature sensors have also been incorporated into adult and baby diapers. The humidity or temperature sensor may undergo a physical or chemical change when liquid comes into contact with the sensor. This, in turn may cause a change in an electrical signal that may be detected by the control unit. The control unit may be pre-programmed to recognize the electronic signal to activate the system before and deactivate after the event. Sensors that may be suitable include impedance sensors, capacitive sensor, piezoelectric sensors or temperature sensors, all of which are commercially available.

The device/system may also comprise a movement sensor for example an oscillator incorporated into the control unit adapted to indicate excessive movement of the patient that may result in noise and may impact the accuracy of the results. The movement sensor may emit a noise or display a light to indicate when significant movement has occurred.

The movement sensor may be used in conjunction with the urination sensors as described above and the movement sensor may only activate when liquid comes into contact with the humidity or temperature sensor. This will only provide an alert if excessive movement occurs during or just after micturition when the data is gathered for analysis.

To detect VUR the position of the electrodes on the patient must remain as still as possible, in particular, during micturition and approximately 10-40, suitably 20-40 seconds before or after micturition (to obtain a base-line measurement). It is important to minimize movement to reduce noise in the system that may lead to measurement errors. The purpose of incorporating a movement sensor is to signal to a person operating the device/system when excessive movement has occurred during measurements and in such cases that; the data may not be suitable for analysis. Young children and babies are often unpredictable and difficult to keep still. If there is excessive movement of the electrode belt, patient noise may be introduced into the signals, which may lead to measurement errors that impact the accuracy of the results.

The movement sensor may measure excessive movement using commercially available components that may include accelerometers, gyroscopes or oscillators.

The impedance measurement module, control unit may use the same configuration as Gaggero et al comprising a current source, signal measurement circuit and signal generator circuit. The signal generator circuit may be connected to the current source and may comprise a waveform synthesis Digital to Analogue Converter (DAC), a filter and an amplifier. The control unit functionality may be implemented using a field-programmable gate array (FPGA) The signal measurement circuit is adapted to measure voltages between the active electronic chip pairs and may comprises amplifiers, filters and an Analogue to Digital Converter (ADC). Alternatively a microcontroller may be used in place of an FPGA.

The control unit may be separable from the belt when it is not actively measuring. When the control unit is separated from the belt it may be connected to the display unit to programme the device/system before monitoring or to extract data following monitoring. The frequency, current injection amplitude and frame rate may be programmed into the device/system. The frequency supplied by the control unit may be in the range 1 to 200 kHz, preferably 50 to 150 kHz, more preferably 50-100 kHz. The injection current supplied by the electronic control unit may be in the range 0.1 and 10 mA, preferably 1 to 7 mA, more preferably 1-4 mA. The injection pattern may be in the range 0 to 15, more preferably 0 or 1. The image rate may be in the range 1 to 50 frames per second. The parameters are selected to optimise the sensitivity of the system for monitoring urine and may vary depending on patient BMI. These values remain within the safe patient auxiliary current. Lower currents should be used for lower frequencies to maintain patient safety.

The control unit may be powered by a portable rechargeable battery such as a lightweight lithium polymer battery or the like or power may be supplied from the mains power supply or optionally via a USB charger or via induction. The control unit may fully enclose the battery and the current source, signal generation and signal measurement circuits. The enclosure may be designed to slide and lock into a housing with magnetic locking or twin button locking either side of the control unit. The enclosure may be square, oblong or a hemi-sphere. The control unit may be designed to lock the electrode belt.

Suitable batteries, connecting cables, processors and viewing monitors will be understood by one of skill in the art from the description herein.

The system may further comprise a user interface or display unit. The user interface or display unit is preferably connectable to the control unit when the control unit is separated from the wearable unit to programme the device/system before monitoring or to communicate data to the processor, before and after measurements are taken. The processor may be integrated into or connected to a display unit that may comprise a smart phone, tablet, laptop or personal computer or the like connected via Ethernet, wireless, Bluetooth or USB or the like to the control unit. Alternatively the display unit and/or all or part of the processor may be integrated into the control unit. The results (e.g. urine volume changes) may be directly displayed on the control unit or display unit.

The processor may incorporate software that may be uploaded to a display unit to allow the user to select input parameters (e.g. frequency, current and image rate) for the impedance measurement module before measurements are taken. After measurements are taken the software may analyse and display results to the user. The output (processed) data may comprise graphs displaying impedance changes. These impedance changes may be further processed and used to construct signal patterns in algorithms or reconstructed images.

The system may be designed to utilize existing bioelectrical impedance technology such as that used for impedance pneumography to produce graphs. Bioelectrical impedance is a non-invasive imaging technology that detects changes in impedance. Electrodes are placed in contact with the skin and a current is applied between at least 2 electrodes and resultant voltages are measured between the same or different electrodes. Bioelectrical impedance can be used to detect and monitor VUR as the changes in bioimpedance are related to volume and pooling of urine in the kidneys and or ureter(s). Bioelectrical impedance systems typically comprise 2-4 electrodes in contact with the patient's skin.

Preferably, the system may be designed to utilize Electrical Impedance Tomography (EIT) to get a distribution of the impedance across a plane. A system includes a plurality of electrodes around a plane in contact with the skin. Current is applied between electrode pairs and resultant voltages are measured from a different set of electrode pairs. The voltage measurements distribution is recorded and analysed to reconstruct an image of the impedance distribution.

A typical EIT system comprises 8-32 electrodes that operate in frames. During each frame the system injects a current with the correct amplitude, measures voltages and controls all the switches in each electrode. For example, if 16 electrodes are used, each frame, i.e. each full set of measurements, is composed of 16*16 voltage measurements.

As an example the current may be injected through the electrode pair (16, 1) first and the resulting voltage differences are measured through all electrode pairs. Once the voltages are measured, the process is repeated by injecting current in the neighbouring pair of electrodes and measuring again in all electrode pairs, until the original position for injecting the current is reached again. All these measurements constitute a data frame, and produce a distribution of the voltages across the plane. The current, frequency, frame rate and injection pattern settings of an EIT system may be defined prior to measurement, these settings may remain unchanged until the end of the measurements.

In the device/system of the invention measured voltage changes are used to reconstruct impedance distribution images across the plane of the kidneys or ureters that reflect changes in volume of urine in the ureters, bladder and/or kidney(s).

Employment of algorithms into the processor may be used for the generation of graphs and reconstructed images; detecting, calculating and quantifying the severity of VUR;

notifying a healthcare provider who may be present with the patient or monitoring the child remotely.

This analysis may be incorporated into processor software designed to be deployed on a variety of desktop and mobile computing systems running different operating systems.

The processor of the EIT system can be used to create a reconstructed image of impedance distribution in the plane of the electrodes. This may be carried out using a linear reconstruction algorithm described by Adler et al 2009. An average impedance distribution image can be created at a base-line (no urination) and an averaged or integrated impedance distribution image created over the urination time. The Impedance change, defined as the change of the mean reconstructed impedance image ($I_{um}$) with respect to a baseline reconstructed impedance image ($I_{bm}$) is evaluated to determine if the patient has VUR. In addition metrics including maximum impedance change and max-to-mean ratio may be extracted from the reconstructed images or raw data and plotted over time to compliment and display supporting data for the impedance distribution images.

The invention also provides a method for detecting urine flow from the bladder to the kidneys comprising recording impedance changes occurring in the ureters, bladder and/or kidneys which indicate changes in volume of urine in the ureters, bladder and/or kidney when impedance changes are detected by bioelectrical impedance and EIT technology.

In the method changes in volume of urine are preferably identifiable by measurements recorded directly before, during and directly after micturition. The measured voltage changes are processed preferably to construct patterns in reconstructed impedance distribution images that indicate changes in volume of urine in the ureters, bladder and/or kidney(s).

The voltage measurement changes during the time point of interest (e.g. during urination) may be compared to a reference value (baseline measurement) before and/or after the time point where measurements during urination may be compared to measurements before and after urination to generate an indication of no VUR or moderate to severe VUR (grades III-V VUR).

DETAILED DESCRIPTION OF THE INVENTION

Figure 1:
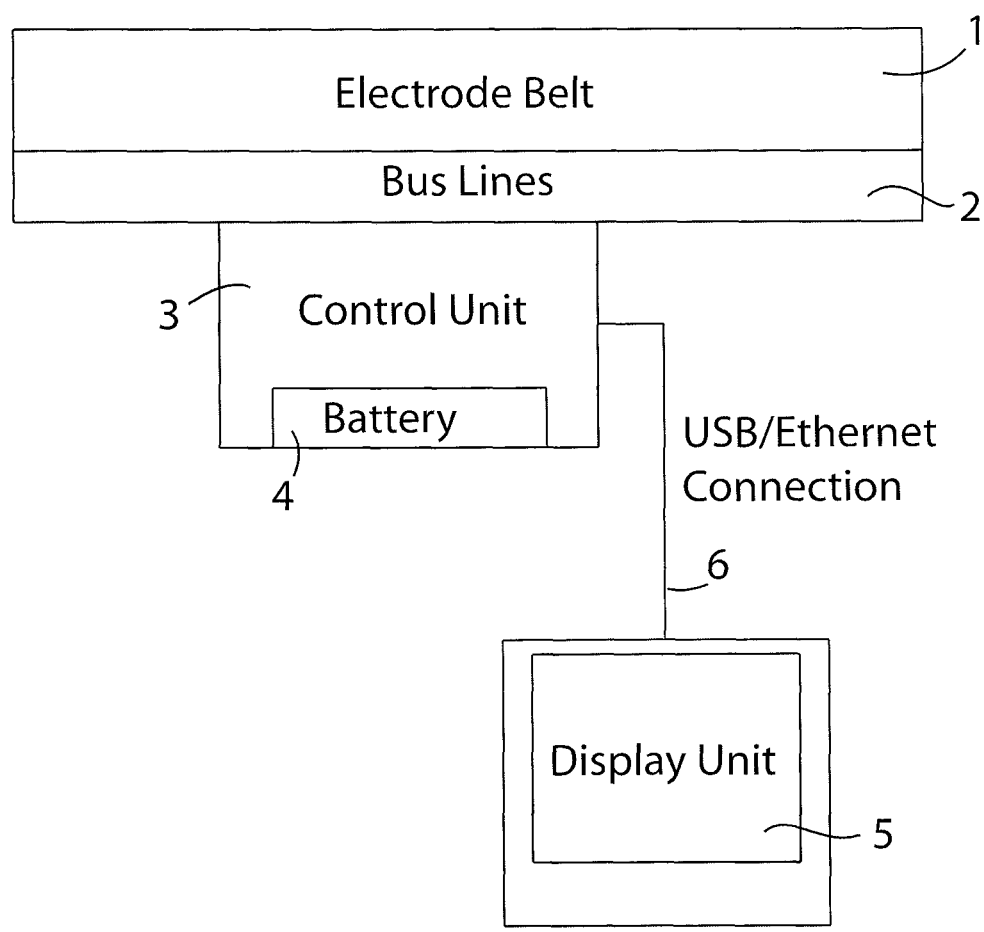
FIG. 1 is a block diagram of a system that comprises the impedance measurement module that may be an electrode belt, bus lines, a control unit, a battery, display unit and connecting cables and a processor that may be incorporated into a display unit.

The impedance measurement module and processor of the device/system of the invention is shown diagrammatically in FIG. 1 to comprise an electrode belt (1), bus lines (2), a control unit (3), a battery (4), display unit (5) and connection interface (6) between the impedance measurement module and the processor. The control unit (3) is attached to a display unit (5) through USB, Wireless, Bluetooth or an Ethernet connection.

Figure 2:
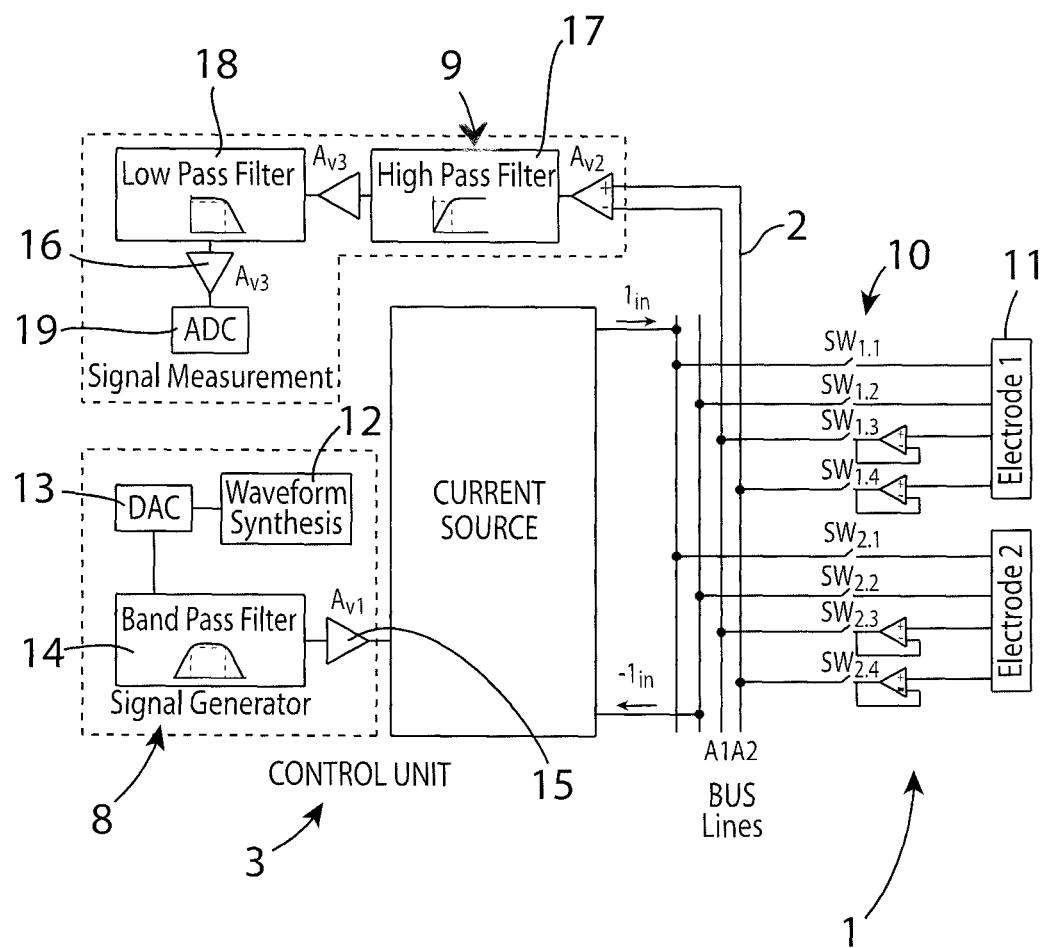
FIG. 2 is a diagram of the impedance measurement module and the steps that may be used to create and measure a signal of the control unit comprising a current source, signal generator and signal measurement system, connecting bus lines and electrode belt comprising active electronic chips connected to electrodes.

FIG. 2 shows diagrammatically the electronics of the circuit of the control unit (3) comprising a current source (7), signal generator (8) and signal measurement system (9), connecting bus lines (2) and electrode belt (1) comprising active electronic circuits (10) connected to electrodes (11). Typically the electrode belt (1) of the invention may contain 8-32 electrodes (11). In this figure the circuits for just two electrodes (11) are provided as an example, where the remaining electrodes may have the same circuitry. Each active electronic circuit (10) contains voltage buffers, switches and a microprocessor to modify the state of the switches. The control unit (3) comprises a current source (7), signal measurement circuit (9) and signal generation circuit (8). The signal generation circuit (8) is connected to the current source (7) and comprises a waveform synthesis (12), a Digital to Analogue Converter (DAC) (13), a band pass filter (14) and voltage amplifier (15). The signal measurement circuit (9), measures voltages between the active electronic circuit pairs and comprises voltage amplifiers (16), low pass (17) and high pass filters (18) and an Analogue to Digital (ADC) converter (19).

Figure 3:
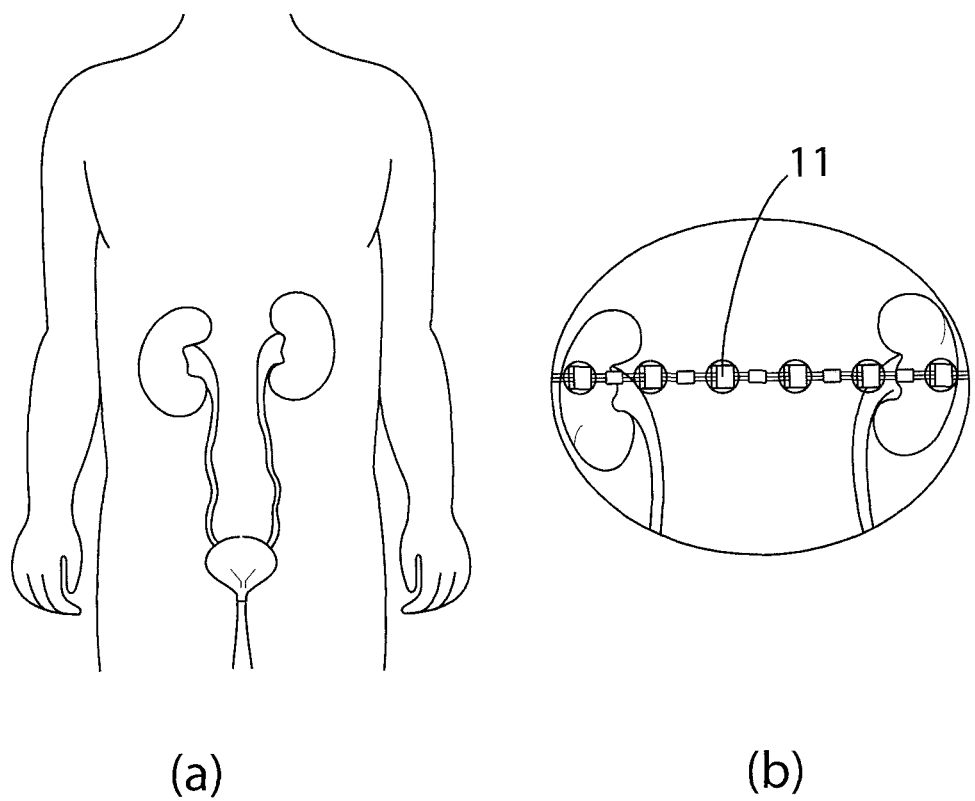
FIG. 3A is an overview of the target anatomy, showing the kidneys, ureters and the bladder.
FIG. 3B shows electrodes positioned over the renal/pelvic area of the kidneys. This is the primary target area for monitoring VUR.

FIG. 3A is an overview of the target anatomy, showing the kidneys, ureters and the bladder. In use the electrode belt (1) will be placed adjacent to the target anatomy to detect changes in volume of urine. Ultrasound imaging or x-ray may be used to identify the exact location of the ureter(s), bladder and/or kidney(s) to make sure that the device is correctly positioned.

FIG. 3B shows electrodes (11) positioned over the renal pelvic area of the kidneys. This is the primary target area for monitoring VUR. During VUR the urine travels to the kidney through the ureters into the renal pelvic area of the kidney.

Figure 4:
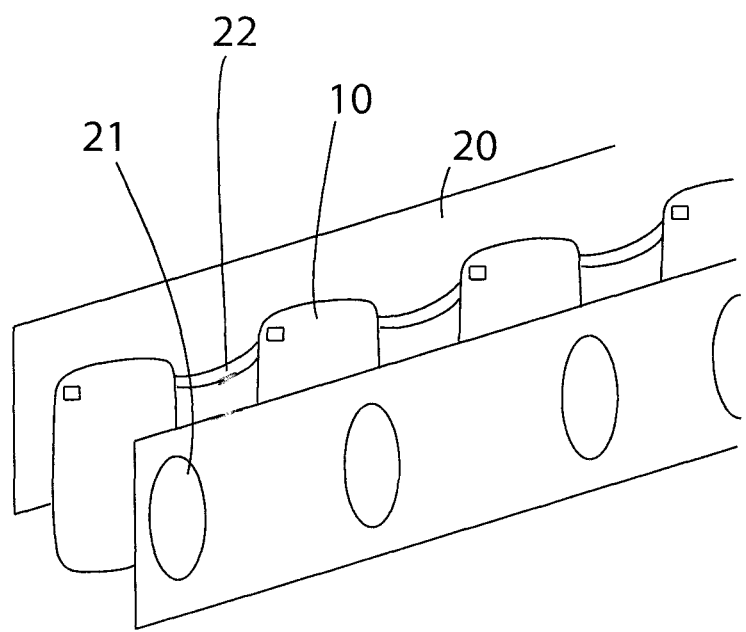
FIG. 4 shows a possible arrangement of the active electronic chips (C) in the electrode belt between 2 layers of material. An outer layer (D) to protect the active electronic chip and an inner layer (B) containing sections of conductive material (A).

The active electronic circuit (10) in the electrode belt (1) are examples of a configuration that may be positioned between two layers of material, as shown in FIG. 4. An outer layer (20) protects the active electronic chips (10) and an inner layer (21) contains sections of conductive material. The outer layer (20) of material is water resistant to protect against ingress of water into electronic components. The inner layer (21) may incorporate an adhesive or high friction material (e.g. vinyl or silicone) to prevent movement and is designed to minimize skin irritation. The inner layer (21) comprises a section of conductive material between sections of non-conductive material that will be in contact with the skin and the active electronic chip (10). The active electronic chips (10) are connected to each other through cables such as flexible flat wire cables or flexible printed cable (22).

Figure 5:
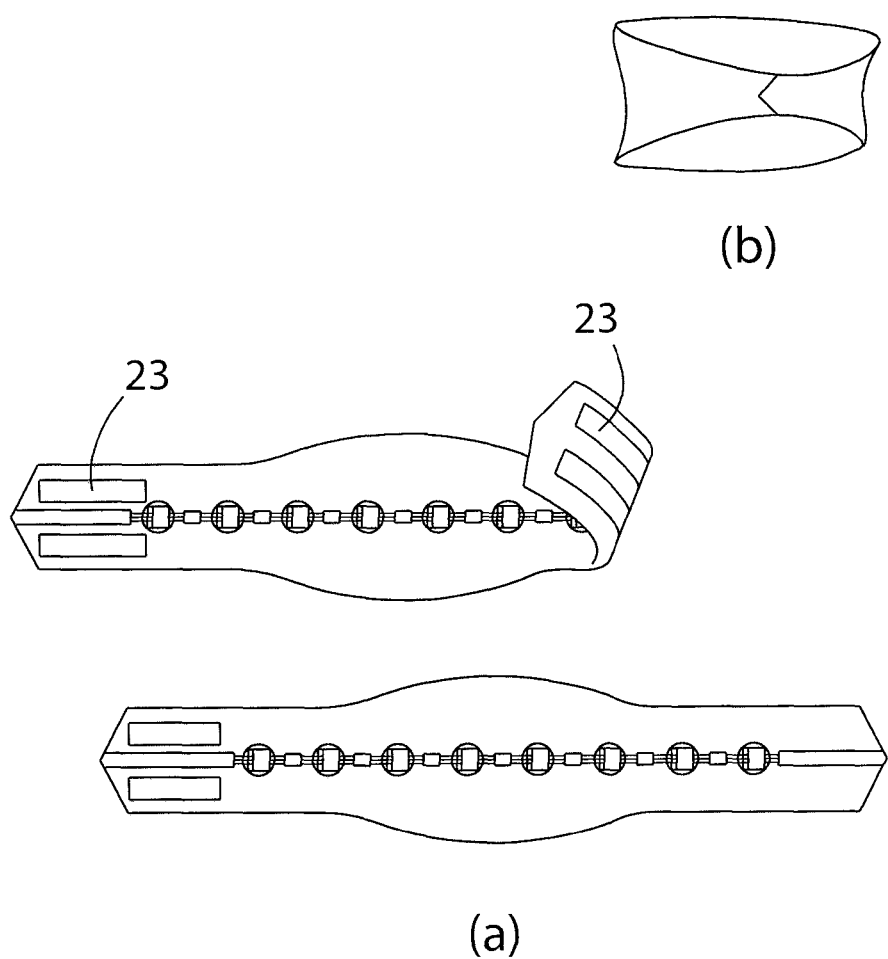
FIG. 5A shows one embodiment of the electrode belt with 8 active electronic chips distributed in a semi-circle arrangement. The belt is thicker at the back than the front, has an inner fabric over the electronic chips and has overlapping Velcro strips for fastening at the front.
FIG. 5B is a perspective view of the embodiment of FIG. 5A.

FIGS. 5A and 5B shows one embodiment of the electrode belt (1) with 8 electrodes (11) distributed in a semi-circular arrangement. The belt (1) is thicker at the back than the front, has an inner fabric layer over the electrodes (11) and has overlapping Velcro strips (23) for fastening at the front. The thicker section at the back provides extra support and the thin section at the front prevents any restriction in breathing.

Figure 6:
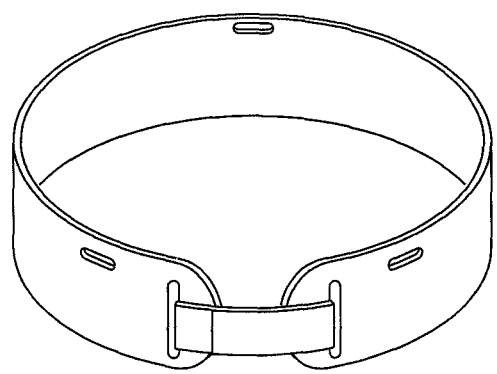
FIG. 6A shows an embodiment of the electrode belt, which has 16 evenly, distributed electrodes and an adjustable strap for fastening the belt. The belt has an adjustable Velcro strip for fastening at the front and an inner fabric covering the electrodes.
FIG. 6B is a perspective view of the embodiment of FIG. 6A.
Figure 6:
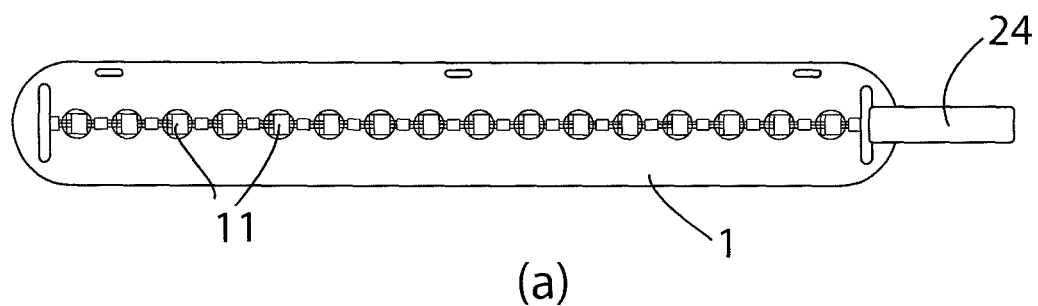

FIGS. 6A and 6B show an alternative embodiment of the electrode belt (1) which has 16 evenly distributed electrodes (11) and an adjustable strap (24) for fastening the belt (1). The belt (1) has an adjustable Velcro strip for fastening at the front and an inner fabric covering the electrodes (11).

Figure 7A:
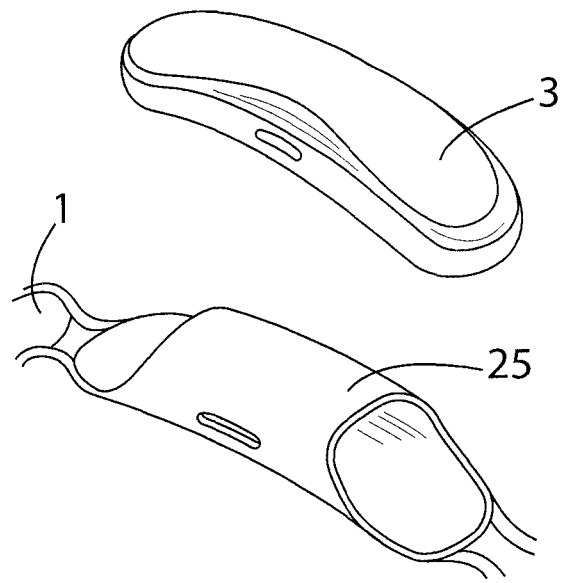
FIG. 7A is a perspective view of an embodiment with an oblong control unit and housing.
Figure 7B:
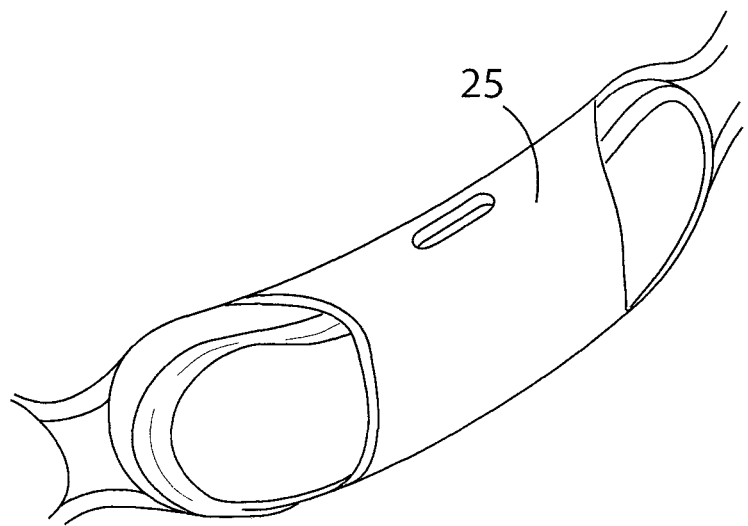
FIG. 7B is a perspective view of the embodiment of FIG. 7A attached for measurement

FIGS. 7A and 7B show a perspective view of an embodiment having an oblong control unit (3) and housing (25). The figure shows the housing (25) and control unit (3) as two separate components. The control unit (3) is separated from the housing (25) when it is not actively measuring. The housing (25) is connected to the electrode belt (1) and provides an electrical contact for the control unit (3) to the belt (1). The control unit (3) may be separated from the housing (25) when it is not actively monitoring the patient and may be connected to the display unit (5) to programme the device/system before monitoring or to extract data following monitoring. The control unit (3) may powered by a portable rechargeable battery such as a light weight lithium polymer battery. The enclosure is designed to slide and lock into the housing (25) with twin button locking either side of the control unit (3).

Figure 8:
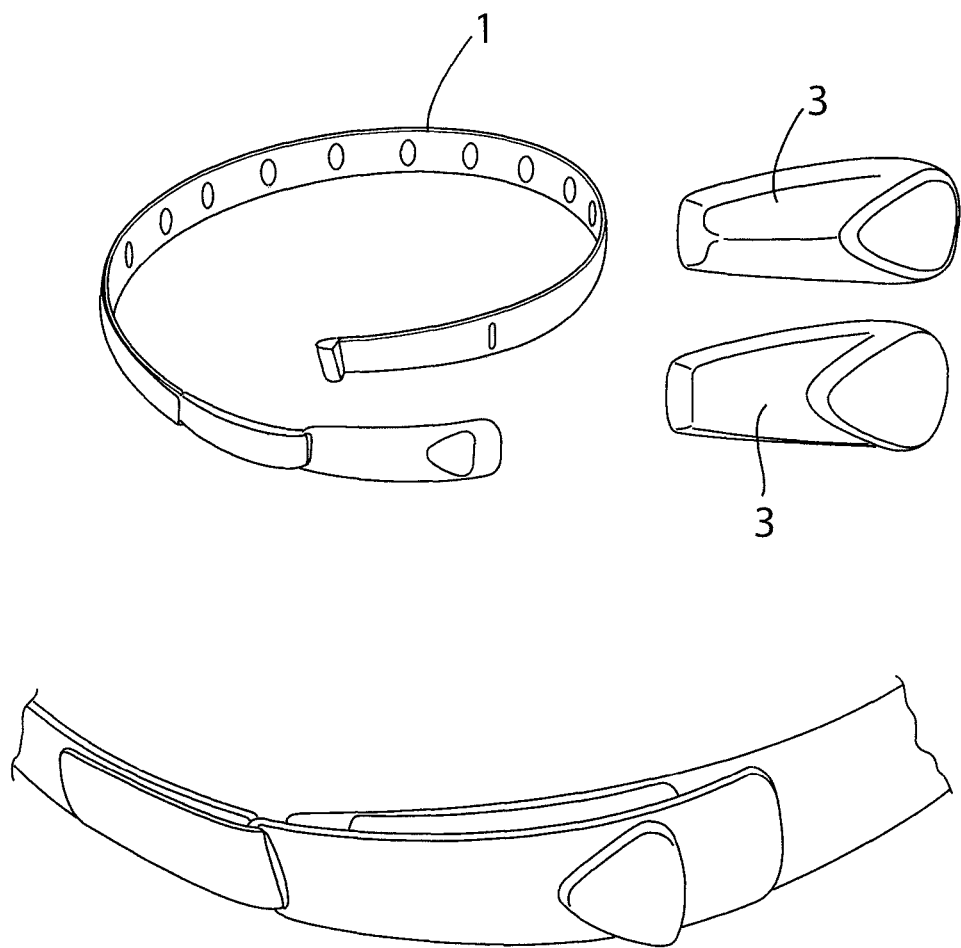
FIG. 8 is a perspective view of an embodiment of the control unit designed to lock the electrode belt.

FIG. 8 shows an embodiment of the control unit (3) designed to lock the electrode belt (1). The belt (1) and control unit (3) are shown as two separate components. The belt (1) also comprises an adjustable Velcro strap (23).

Figure 9:
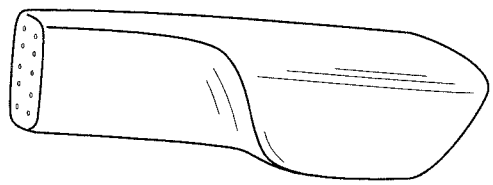
FIG. 9 is a perspective view of an embodiment of an alternative shape control unit with the same locking mechanism as FIGS. 8A and B.
Figure 9:
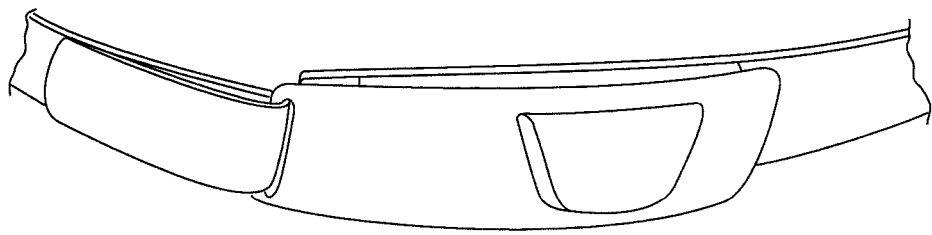

FIG. 9 shows an embodiment of an alternatively shaped control unit (3) with the same locking mechanism and control unit (3) configuration as FIG. 8.

Figure 10A:
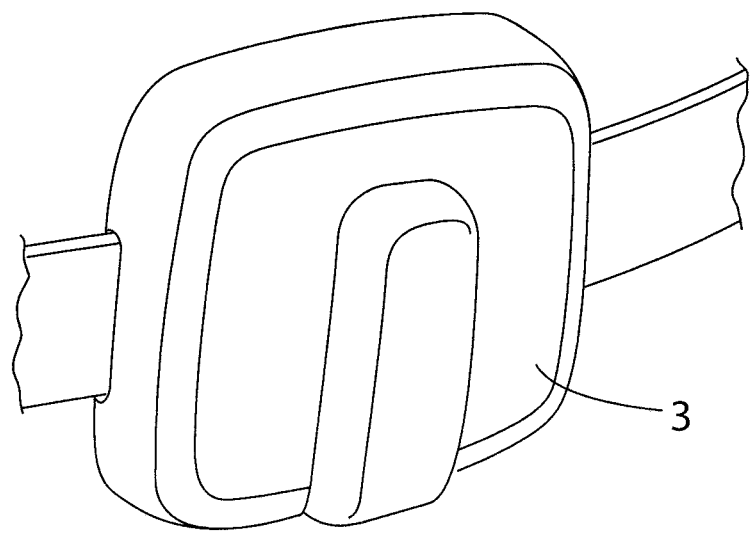
FIG. 10A is a front facing perspective view of an embodiment of a square control unit that may be connected to the belt through fixed loops in the control unit.
Figure 10B:
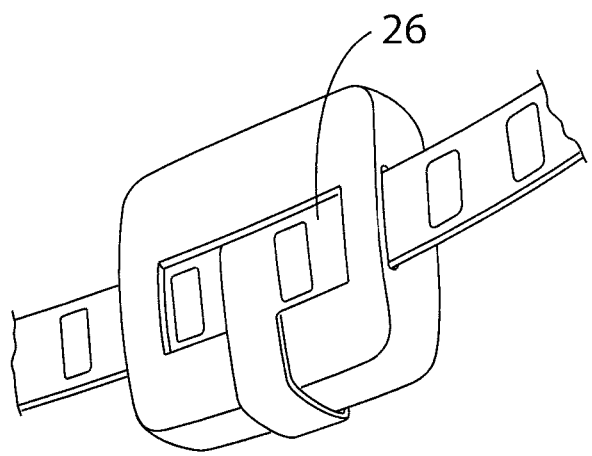
FIG. 10B is a rear facing perspective view of an embodiment of a square control unit that may be connected to the belt through fixed loops in the control unit.

FIG. 10A shows an embodiment of a square control unit (3) that may be connected to the belt (1) through fixed loops (26) in the control unit (3). The square shape control unit (3) reduces its size in any one direction to prevent any restriction in movement of the patient.

Figure 11A:
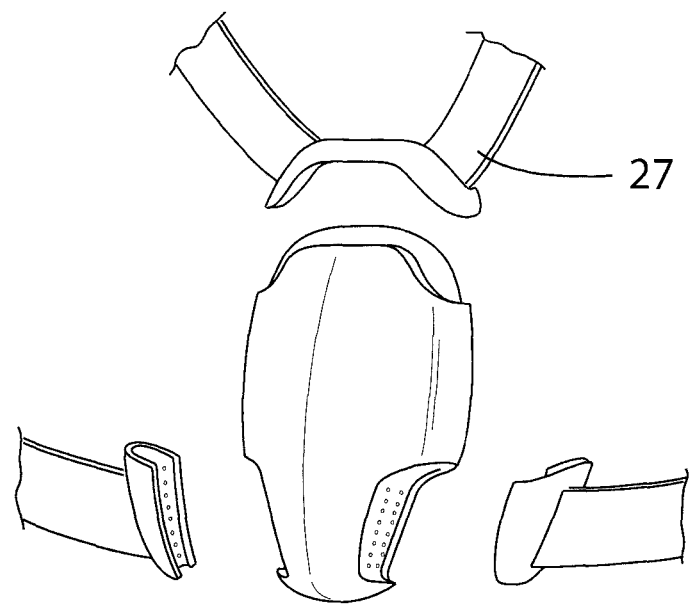
FIG. 11A is a perspective view of an embodiment of a vertically positioned control unit, where it is connected to the belt on each side and a neck harness from the top for support.

FIG. 11A shows a vertically positioned control unit (3), which is connected to the belt (1) on each side and a neck harness (27) from the top for support. The control unit (3) is connected to the belt (1) on each side and a neck harness from the top for support. The neck strap may provide support and balance of the control unit (3) and position it remotely from the belt (1), potentially reducing interference with electrode contact.

Figure 11B:
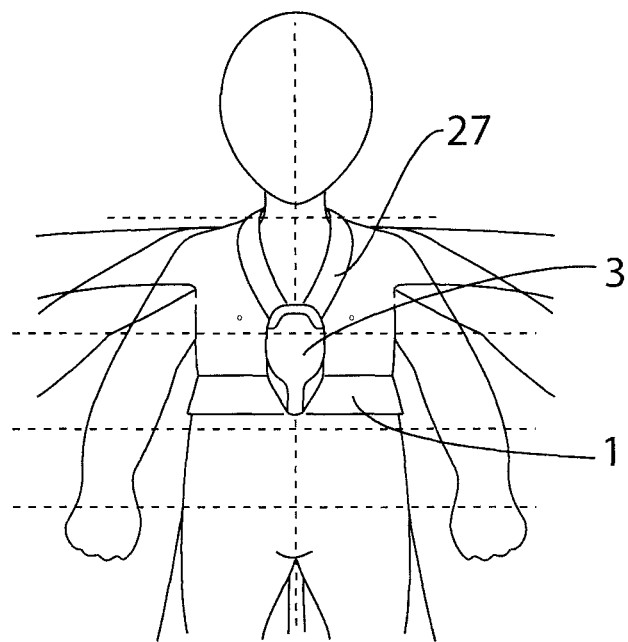
FIG. 11B is an embodiment of the invention in which the control unit is attached to a belt and a harness for support around the neck. The image shows the device worn by a patient.

FIG. 11B shows an embodiment of the invention in which the control unit (3) is attached to a belt (1) and a harness (27) for support around the neck, as worn by a patient.

Figure 12A:
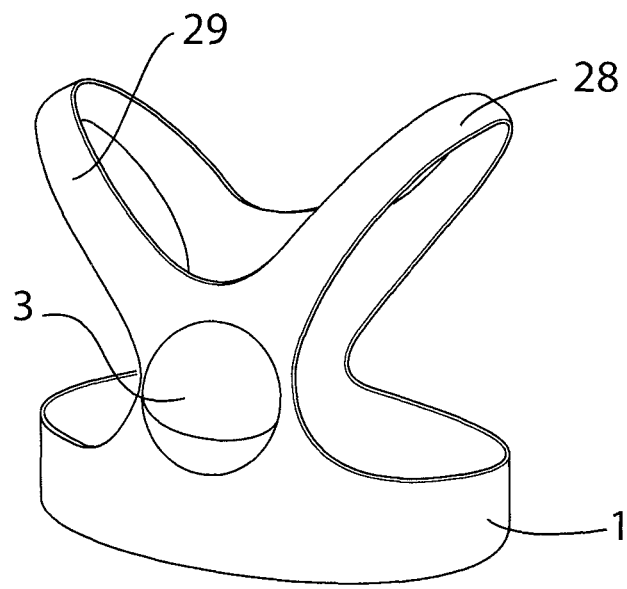
FIG. 12A is a perspective view of an embodiment of the invention in which the control unit is a hemi-sphere and is inserted into a vest.
Figure 12B:
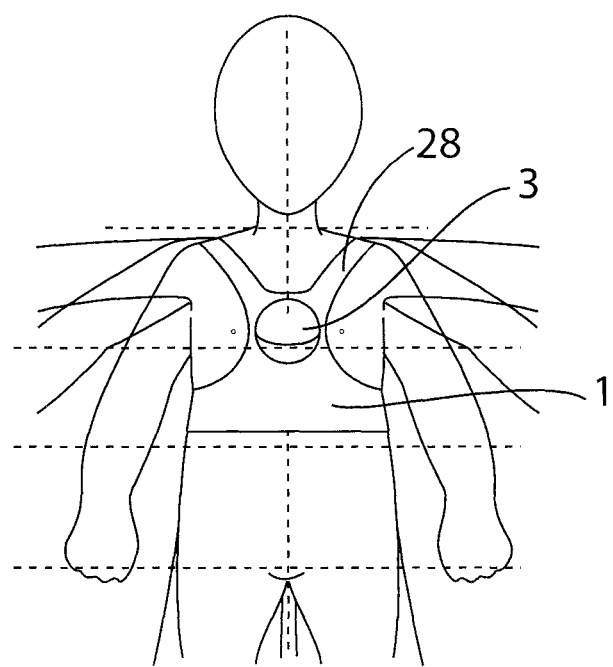
FIG. 12B is an embodiment of the invention in 12A worn by a patient.

FIGS. 12A and B show an embodiment of the invention in which the control unit (3) is a hemi-sphere and is inserted into a vest (28). The electrode belt (1) is integrated into the vest (28) with support straps (29) around the shoulder to maintain the position of the electrode belt (1) and support the control unit (3). The electrode belt (1) is connected to the bottom of the vest (28). The control unit (3) can be placed in the center of the chest or on the back. The vest (28) will provide support and balance of the control unit (3) and position it remotely from the belt (1), potentially reducing interference with electrode contact.

Figure 13A:
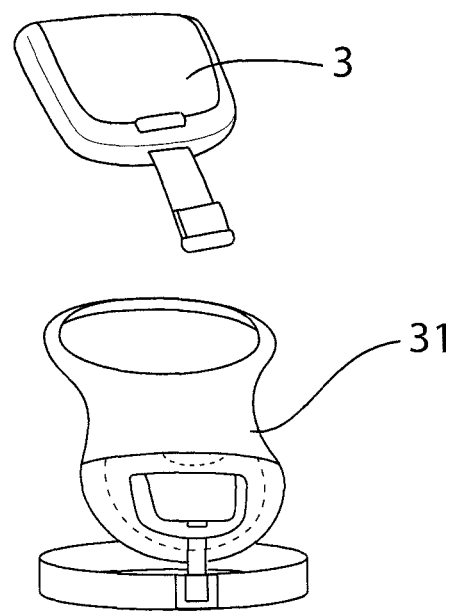
FIG. 13A is a perspective view of an embodiment of the electrode belt and control unit in which the control unit is inserted into a bib and connected to the belt.
Figure 13B:
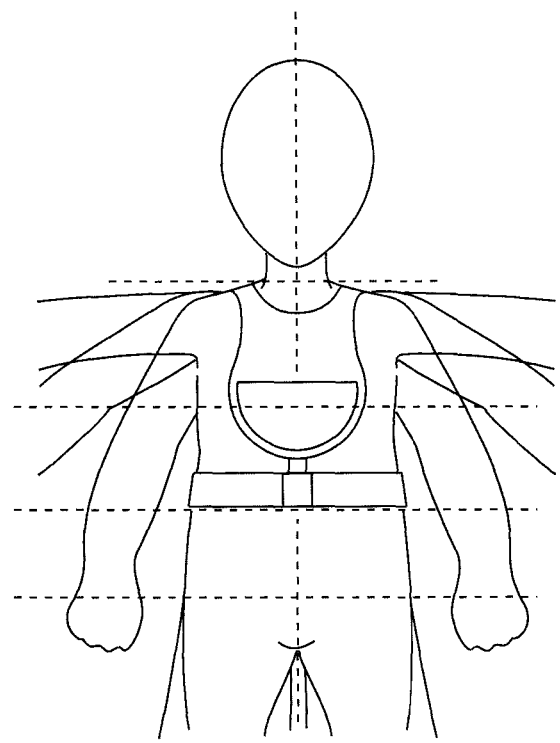
FIG. 13B is an embodiment of the invention in 13A worn by a patient.

FIGS. 13A and B show an embodiment of the electrode belt (1) and control unit (3) in which the control unit (3) is inserted into a bib (30) and connected to the belt (1). The bib (30) is placed around the neck of the patient to support the belt (1). The control unit (3) has a single connection and is placed in the pocket (31) of the bib (30). The bib (30) provides support and balance for the control unit (3) and positions it remotely from the belt (1), potentially reducing interference with electrode contact.

Figure 14A:
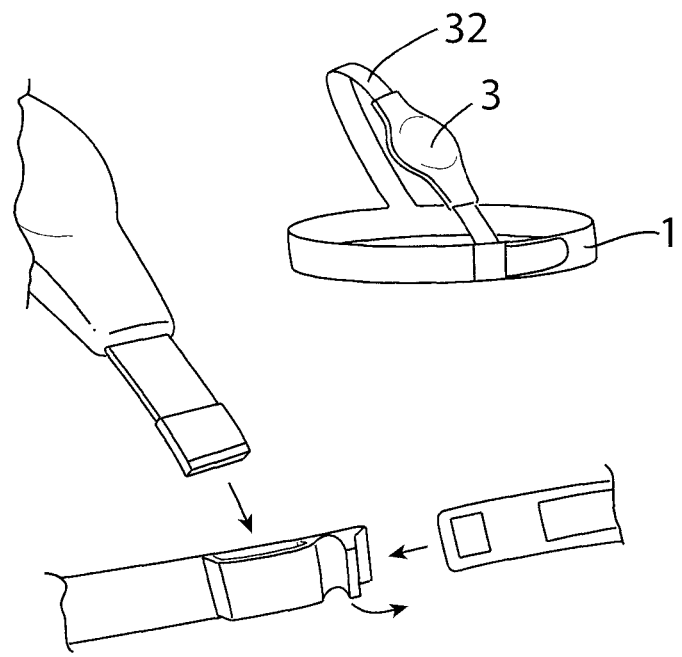
FIG. 14A is an embodiment of the invention in which the control unit is oblong and is attached to the front and back of the belt at an angle so that the control unit sits across the chest of the patient.
Figure 14B:
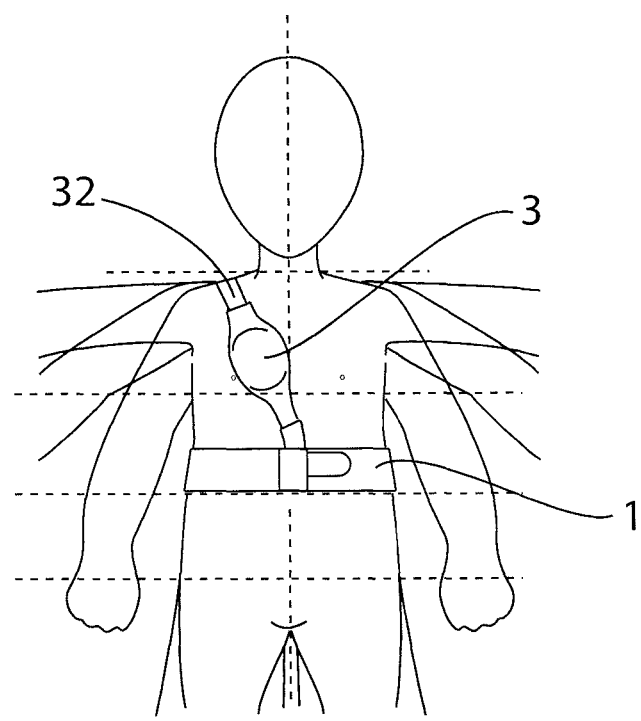
FIG. 14B is an embodiment of the invention in 14A worn by a patient.

FIGS. 14A and B show an embodiment of the invention in which the control unit (3) is oblong and is attached to the front and back of the belt (1) at an angle so that the control unit (3) sits across the chest of the patient. A strap (32) is passed through the control unit (3) and around one shoulder of the patient diagonally across the body. This supports and balances the control unit (3) away from the belt (1), preventing interference with electrode contact.

Figure 15A:
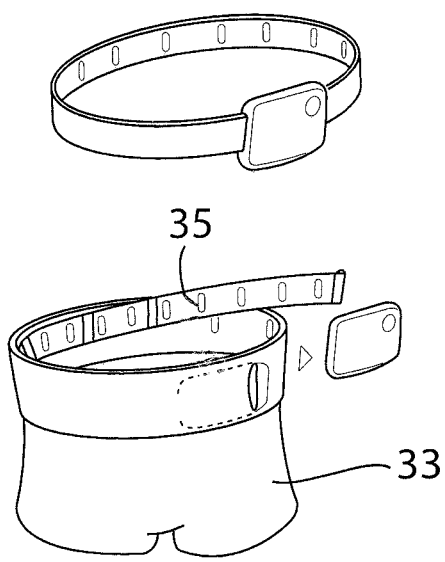
FIG. 15A is an embodiment of the invention in which the belt and control unit are incorporated into shorts.
Figure 15B:
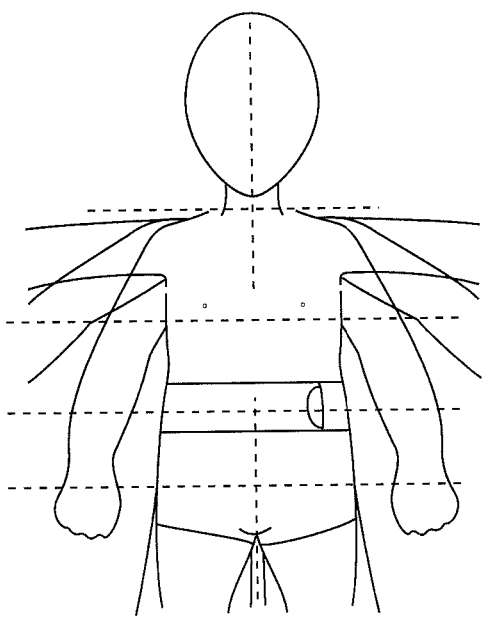
FIG. 15B is the embodiment of FIG. 15A when worn by a patient.
Figure 16:
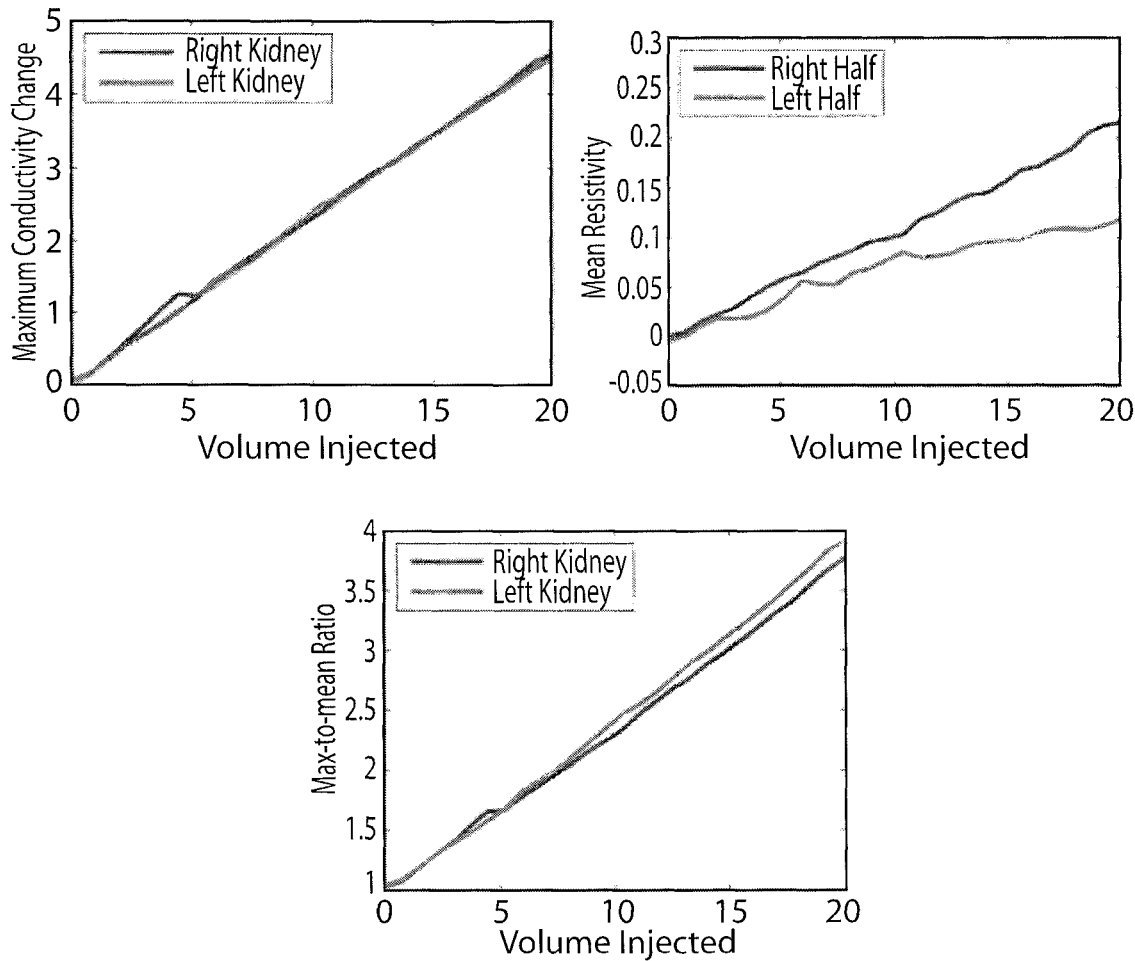
FIG. 16 are graphs developed using an in-vitro bench top model of the kidneys. The graphs illustrate maximum impedance change and max-to-mean ratio, resistivity index and mean resistivity.
Figure 17:
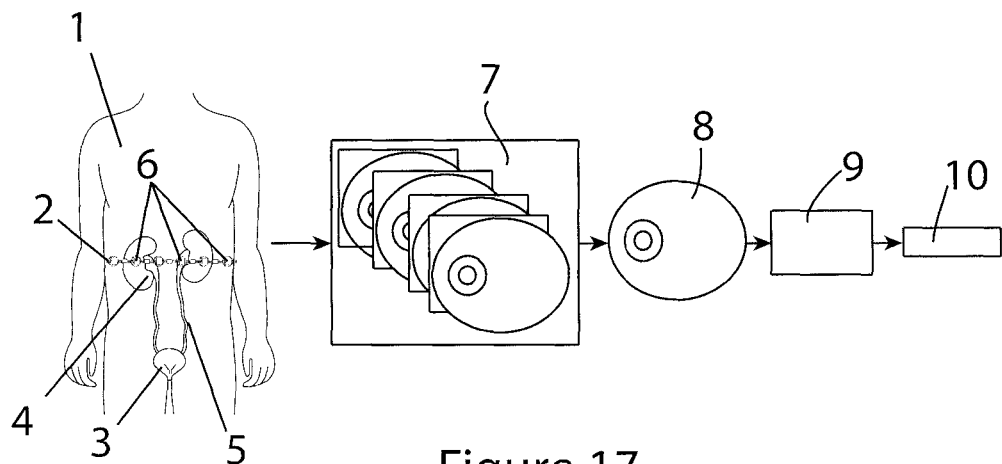
FIG. 17 detail the steps used to measure and process an impedance distribution image to establish if urine is travelling to the kidneys at a particular time period.

FIGS. 15A and B shows an embodiment of the invention in which the belt (1) and control unit (3) are incorporated into shorts (33). The shorts comprise absorbable material or may be worn over a nappy to allow for urination without removal of the shorts (33). There is a pocket (34) in the shorts (33) to hold the control unit (3). This will support and balance the control unit (3) away from the belt (1), preventing interference with electrode contact. The electrode belt (1) is supported by inner loops (35) around the waistband to secure the electrode belt (1). FIG. 17 shows the steps the system uses to detect urine in the kidneys or ureters using EIT. The steps involve correctly positioning the electrodes around the plane of the body at the level of the kidneys. Using the impedance measurement module to gather impedance measurements over a period of time. The processor then receives the impedance measurements from the impedance measurement module and analyses the measurements to create a series of impedance distribution images (7) gathered for each second (at least) during the time period using the impedance measurement module. Each impedance distribution image corresponds to the volume of liquid flowing to the kidneys at a particular time point. The impedance distribution images are gathered and processed (7) and an average impedance distribution image (8) is output to provide the average change that occurs at a baseline and during urination. The average impedance distribution images during urination are filtered (9) and a comparison is made to a base-line image obtained before or after urination. A display unit (10) provides the results to the user, this information is used to indicate if VUR is occurring.

Figure 18:
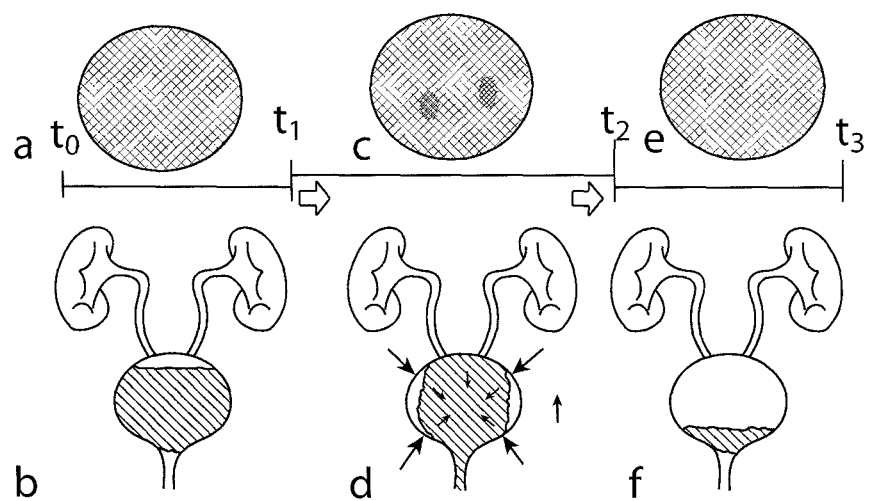
FIGS. 18 (a) to (f) represent the steps used to process the impedance distribution image and the time period when data is collected, i.e. when the bladder is full (e.g. just prior to micturition), during periods of elevated pressure below the kidneys resulting in VUR (e.g. during micturition) and after the bladder is empty.

FIG. 18 further shows the steps and time-frame when the images are measured and analysed. The average impedance distribution image may be obtained before (11), during (12) and after (13) urination (15). At times 0 s (t0)—when the bladder is full (14) and the patient will need to void. T0 is recorded as a time-stamp in the measurements. The device/system may be activated prior to this or at this point in time. Once voiding commences (15) a timestamp t1 is recorded to represent the beginning of urination. The average of the impedance distribution images obtained between t0 and t1 is output (11).

Figure 19:
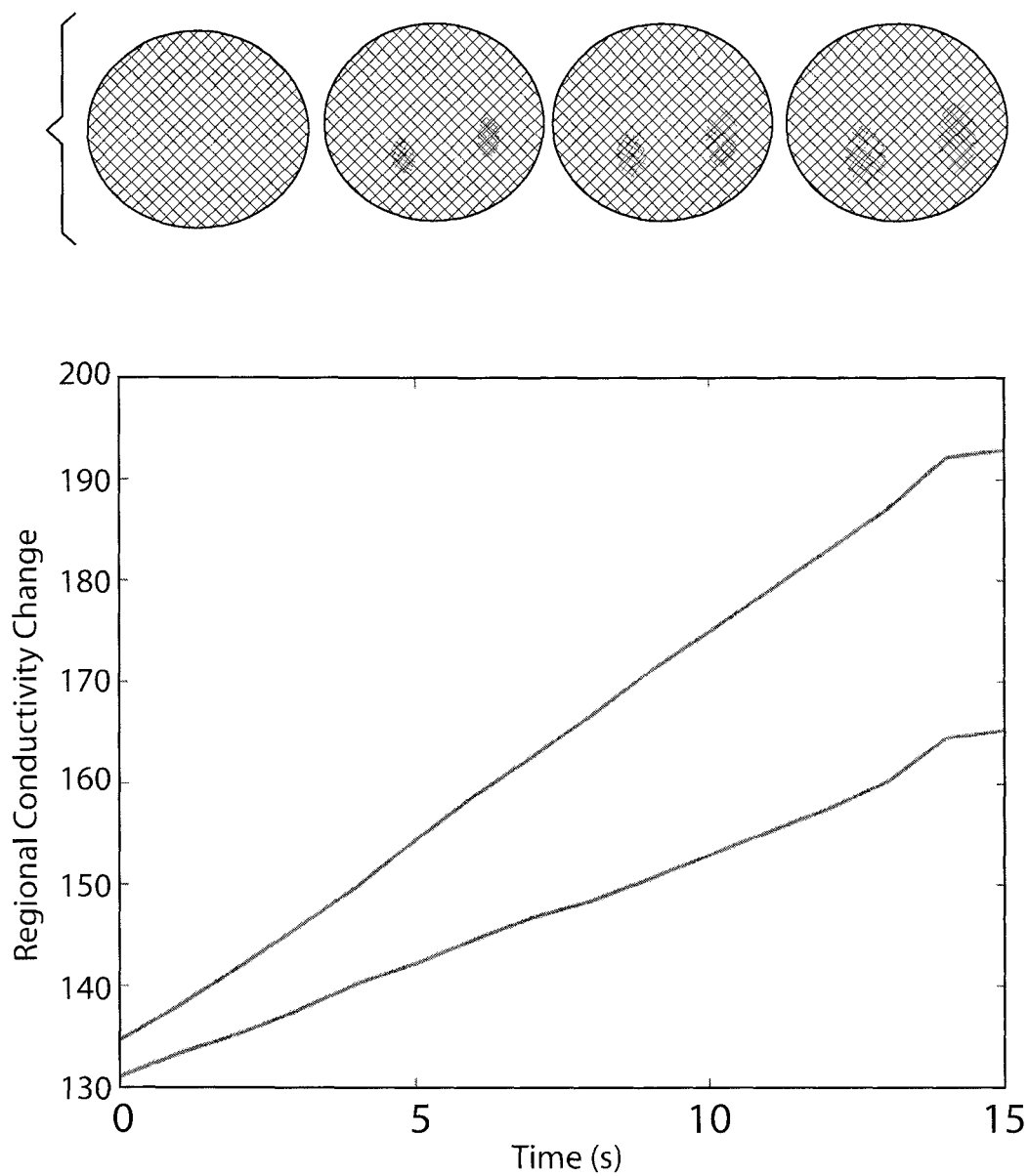
FIG. 19 represents the changes observed during the pre-clinical study in a porcine model when 10 ml of liquid is injected over 15 seconds. The graph displays the regional conductivity change this is the mean impedance in the region of interest during the time period.

Timestamp t2 represents the end of voiding the average impedance distribution image between t1 and t2 is output (12). Timestamp t3 is established at the end of measurements. The average EIT impedance distribution image between t2 and t3 (13) is output. The images (11,12,13) are compared to determine if urine is travelling towards the kidneys. In children that are not toilet trained a physician may check if the bladder is full (e.g. using ultrasound), external pressure may be placed on the bladder, simulating bladder contraction (e.g. voiding). FIG. 19 represents the results from the pre-clinical study. During the pre-clinical studies a porcine model was used to simulate VUR using open retrograde ureteric infusion. A correlation between reflux volume and bladder capacity was used to establish reflux volume. This is estimated to be between 10% and 15% of bladder capacity. Bladder volume can be estimated using (age in years+2)×30 mL. As a result, a volume between 8 and 30 ml was considered realistic to simulate VUR. A volume of 10 ml was selected as appropriate acceptance criteria for the study based on the minimum average VUR volume children age 6 month to 2 years. The impedance distribution images are shown in figure. A series of images were taken at different time points before and during infusion into the kidneys. The graph displays the change in regional conductivity over time.

All of the embodiments of the electrode belt (1) of the invention contain electrodes (11), The electrodes (11) do not touch each other and comprise discrete portions of highly conductive material (average surface resistivity of 8-105 Ohm/sq) that will come into contact with the skin. The electrodes (11) will be in contact with the skin. The electrode arrangement comprises multiple electrodes (11) on the body surface adjacent to the area of interest i.e. the bladder, ureter(s) or kidney(s) of the patient. The electrodes (11) are in direct conductive contact or capacitively coupled to the body surface. Suitable electrode (10) materials for use in the invention include gold-plated copper, stainless steel or conductive textile electrodes attached to the electrode circuit may also be suitable. The electrode material may be a conductive microfiber nonwoven metamaterial or Pyrrole conductive polymer. The wearable unit may comprise electrodes secured directly to the body for conductive contact with a non-conductive solution or gel layer such (e.g. ultrasound gel or water) between the skin and the electrodes to reduce the impedance of the skin. In addition to the gel layer an adhesive or high friction material (e.g. silicone, rubber or vinyl) on the inner surface in contact with the patient's skin may also act to increase the coefficient of friction between the skin and the belt to help secure the belt in position.

A typical EIT system comprises 8-32 electrodes that operate in frames. During each frame the system injects a current with the correct amplitude, measures voltages and controls all the switches in each electrode. For example, if 16 electrodes are used, each frame, i.e. each full set of measurements, is composed of 16*16 voltage measurements.

As an example the current may be injected through the electrode pair (16, 1) first and the resulting voltage differences are measured through all electrode pairs. Once the voltages are measured, the process is repeated by injecting current in the neighbouring pair of electrodes and measuring again in all electrode pairs, until the original position for injecting the current is reached again. All these measurements constitute a data frame, and produce a distribution of the voltages across the plane.

The impedance measurement module may comprise electrodes with integrated electronics (e.g. chips) designed to measure and buffer the voltages as close as possible to the patient to minimize problems that may arise due to the analogue transmission of signals on high impedance lines. Switches, buffers and a microprocessor may be used to control the current injection pattern between electrode pairs. This circuit is depicted in FIG. 2. The active electronic circuits (chips) (10). Where a chip is used each active electronic chip has switches to multiplex the signals received and transmitted to the control unit. For example, the system may have two switches for injecting and sinking a current ($SW_{1,1}$ and $SW_{1,2}$, respectively) and two switches for buffering voltage and transmitting it to the control unit via bus analogue lines A1 and A2 ($SW_{1,3}$ and $SW_{1,4}$) (See Electrode 1 in FIG. 2).

The voltage buffer is used to transfer a voltage from a first circuit with a high output impedance level, to a second circuit with a low input impedance level. During each measurement two electrodes become active. Each of the working electrodes transmits the buffered signal to one of the two bus lines (A1 or A2). The voltage difference between lines A1 and A2 is calculated by the control unit and the analogue signal is transformed to a digital signal.

The active electronic chips may also comprise a microprocessor or a Read-Only-Memory (ROM) to control their state (i.e. which switches are opened or closed at each instant) and a memory to store a table with all the states of the active electronic chips. In addition, a table pointer may be required to point to the current state. Each active electronic chip has exactly the same table, but the pointer starts at different locations in the table for each frame. The state pointer changes as a clock pulse is sent from the digital part of the control unit (through a synchronization line), applying the corresponding configuration to the switches. When the state pointer reaches the end of the table, it loops back to the beginning of the table. Since the pointer starts at different locations, this implementation requires that each active electronic chip is individually programmed.

For the end-product, each active electronic chip comprises buffers, switches and a microprocessor/ROM implemented in a circuit board, this may be arranged in a single (Printed Circuit Board) PCB to minimize the size of the system/device. The active electronic chips may then be attached directly to the electrode material through soldering or similar method.

The entire system is controlled by the impedance measurement module control unit, a central system responsible for electrode management, signal acquisition, current generation and communication with the user.

The entire process for signal acquisition as depicted in FIG. 2, based in the method followed by Gaggero at al.:

The current source may comprise an operational amplifier or transconductance amplifiers examples include a floating current source with transformer coupling, operational transconductance amplifiers current source, supply-current sensing current source, three-operational-amplifier current source or howland's current source.

The impedance within the kidney may be inferred from voltage measurements taken between electrodes at the surface of the body adjacent to the kidney(s) or ureter(s) within at a given time point.

The device/system may take measurements before urination, during urination and after urination. The voltage readings before and or after urination are used as baseline measurements and are subtracted from the readings during urination to determine if an increase in voltage and hence impedance has occurred in the kidney(s) or ureter(s). If an increase in impedance has occurred, the patient is likely to be suffering from VUR.

Alternatively, if residual urine flows from the kidneys into the bladder after urination and changes the impedance in the bladder the patient may be suffering from VUR. Likewise, the impedance within the bladder may be inferred from voltage measurements taken between all active electrode pairs at the surface of the body within one data frame, at a given time point.

The processor may use software algorithms and classifiers to analyse the data obtained from the measurement module of the device/system. The algorithms can be used to optimise the accuracy of the results produced by impedance measurement module, used to detect changes in impedance and volume of urine in the ureters, bladder and/or kidney(s). Alternatively the display unit may be incorporated into the system as a portable embodiment of the system. There are a number of Electrical Impedance Tomography Devices available for commercial use. These devices are typically used to monitor lung function in critically ill patients. Results for these devices are displayed as real-time images and impedance change waveforms and numeric parameters that are derived from these images.

The Graphical output from reconstructed images (detailed below) provide the user with additional information that optimises the sensitivity and specificity in the region of interest. Metrics including maximum impedance change and max-to-mean ratio can be extracted from the impedance distribution images and plotted over time.

Maximum Impedance Change in a Region of Interest describes the maximum impedance response in a selected region of interest (e.g. at the location of the kidneys) within the distribution image over time. A linear increase represents increasing volume of urine in the region of interest. This metric may provide improved detection of small changes in impedance in the region of interest.

Max-to-Mean Ratio describes the maximum response in the image divided by the average response in the image. This metric may provide more detailed information relating to the contrast between the region of interest and the background in the reconstructed image. Extracting metrics such as maximum conductivity change in the selected region of interest (ROI) (around the kidneys) and max-to-mean ratio to analyse trends in conductivity change and image quality. Particularly, Max-to-mean ratio could be used to detect images with significant artefacts that may be discarded from analysis—e.g. if the conductivity change in the ROI is increasing with time but the max-to-mean ratio is below a certain threshold in some frames, this means that the conductivity change in the kidneys in those frames are not significantly higher than conductivity changes elsewhere, which means that those images are likely to contain significant artefacts and should be discarded.

The following details how voltage measurements may be analysed by the processor: voltage measurements over time are translated into a reconstructed image of impedance distribution in the plane of the electrodes. This may be carried out using a linear reconstruction algorithm described by Adler et al 2009. An average impedance distribution image is created at a base-line (no urination) and impedance distribution images are gathered (approximately 1 image per second) during urination as a series of reconstructed images ($I_{u1}, I_{u2}, I_{u3}$ etc.). This series of impedance changes (during urination) may be averaged or integrated over the urination time to create a single mean reconstructed impedance image ($I_{um}$). The mean image ($I_{um}$), series of reconstructed images ($I_{u1}, I_{u2}, I_{u3}$ etc.) and the average base-line reconstructed impedance image ($I_{bm}$) may be filtered to remove image artefact and isolate the kidney region. The series of images are visually analysed ($I_{u1}, I_{u2}, I_{u3}$ etc.) to determine if the impedance in the region around the kidneys is increasing over time during urination. Impedance change, defined as the change of the mean reconstructed impedance image ($I_{um}$) with respect to a baseline reconstructed impedance image ($I_{bm}$) is evaluated to determine if the patient has VUR. The images are ranked to determine the quality of the image and indicate the likelihood that the patient has VUR. A ranking of 3, 4 or 5 indicates that a significant volume of urine is travelling to the kidney and indicates that the patient has VUR. The following are the rankings used and description of the criteria applied to the reconstructed image.

| Reconstructed Image Rating | Description of criteria relating to reconstructed images |
|---|---|
| 5 | For each reconstructed image during urination ($I_{u1}$, $I_{u2}$, $I_{u3}$ etc.): impedance changes in the around kidney increase approximately linearly over time. When the average impedance image ($I_{um}$) is compared to the base-line image ($I_{bm}$), there is an area of isolated change around the area of the kidney and little significant noise is present elsewhere - region of noise around the kidney < than region(s) of impedance change elsewhere. |
| 4 | For each reconstructed image during urination ($I_{u1}$, $I_{u2}$, $I_{u3}$ etc.): impedance changes in the around kidney increase approximately linearly over time. When the average impedance image ($I_{um}$) is compared to the base-line image ($I_{bm}$), there is an area of isolated change around the area of the kidney and significant noise is present elsewhere - region of noise around the kidney > than region(s) of impedance change elsewhere. |
| 3 | For each reconstructed image during urination ($I_{u1}$, $I_{u2}$, $I_{u3}$ etc.): impedance changes in the around kidney increase over time. When the average impedance image ($I_{um}$) is compared to the base-line image ($I_{bm}$), there is an area of non-isolated change around the area of the kidney visible and significant noise is present elsewhere and region(s) of impedance change exist elsewhere |
| 2 | Impedance changes around kidney possible intermittently, no direct conclusion |
| 1 | No indication of impedance changes around kidney |

The following methods may be used to filter the image to remove artefacts and isolate the region around the kidney to improve the accuracy of the results:

(i) Obtain a priori—a prior knowledge of the location of the kidney. This can be done by using historical data e.g. CT scans of children of different ages and correlate the location of the kidney to BMI (ii) image processing, this may include increasing image resolution (from 64×64 pixels to 256×256 pixels) so it becomes less 'pixilated' or (iii)
Using a Blur Kernel The "average impedance distribution images" during urination are used to identify the positions of each kidney, defined as the "regions of interest". A Gaussian blur kernel is created to replicate the region of interest for each image, according to the Gaussian blur formula:

$$\left(\frac{1}{2*\pi*\sigma^2}\right)*\exp\left(-\frac{(x-xKidney)^2+(y-yKidney)^2}{2*\sigma^2}\right)$$

x and y represent the coordinates of each pixel, xKidney and yKidney represent the central location within the region of interest and σ is the standard deviation of the Gaussian distribution that represents the size of the region of interest. Two images representing the Gaussian blur kernels (one for each kidney—"region of interest") are overlaid to obtain a single combined image with two kernels, representing each kidney. The values of each pixel in the combined image are scaled from 0 and 1 and represent a "filter image". The "filter image" is multiplied by the "average impedance distribution image" (to filter out image artefacts and isolate the kidney region for each infusion. This method may also be implemented for each impedance distribution image in the series.

Under current practice, generally all children presenting with UTIs would be referred for VCUG imaging to detect VUR. If the device/system of the present invention were used to rule out those without VUR (70%) and those with mild VUR (22%), in total 92% of patients that would previously have been considered for VCUG imaging, would not need to be referred.

Although the invention is described herein with reference to specific embodiments, the invention is not intended to be limited to the details shown. Rather, various modifications may be made in the details within the scope and range of equivalents of the claims and without departing from the invention.

The words "comprises/comprising" and the words "having/including" when used herein with reference to the present invention are used to specify the presence of stated features, integers, steps or components but does not preclude the presence or addition of one or more other features, integers, steps, components or groups thereof.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination.

REFERENCES

Adler, A., et al. "Monitoring changes in lung air and liquid volumes with electrical impedance tomography." Journal of Applied Physiology 83.5 (1997): 1762-1767.

Gaggero P O, Adler A, Brunner J, Seitz P. Electrical impedance tomography system based on active electrodes. Physiol Meas. 2012; 33(5):831-47.

The invention claimed is:

1. A method for detecting urine flowing from the bladder to the kidney(s) or ureter(s) in a subject, the method comprising recording conductivity changes occurring in the ureters, bladder and/or kidneys which indicate changes in volume in the ureters, bladder and/or kidney wherein conductivity changes are detected by bioelectrical impedance or electrical impedance tomography and these volumes being compared to control values to indicate the presence or absence of VUR in the test subject, wherein measured voltage changes are used to construct images or graphs that indicate changes in volume of urine in the ureters, bladder and/or kidney(s).

2. A method for detecting urine flowing from the bladder to the kidney(s) or ureter(s) in a subject, the method comprising recording conductivity changes occurring in the ureters, bladder and/or kidneys which indicate changes in volume in the ureters, bladder and/or kidney wherein conductivity changes are detected by bioelectrical impedance or electrical impedance tomography and these volumes being compared to control values to indicate the presence or absence of VUR in the test subject, wherein measurements are taken as bladder pressure increases during micturition or filling, or as bladder pressure increases as pressure is applied to the abdomen and hence to the bladder, either manually or by the system itself.

3. A method for detecting urine flowing from the bladder to the kidney(s) or ureter(s) in a subject, the method comprising recording conductivity changes occurring in the ureters, bladder and/or kidneys which indicate changes in volume in the ureters, bladder and/or kidney wherein conductivity changes are detected by bioelectrical impedance or electrical impedance tomography and these volumes being compared to control values to indicate the presence or absence of VUR in the test subject, wherein data is collected during micturition and compared to a baseline measurement taken when no micturition is occurring.

4. A method for detecting urine flowing from the bladder to the kidney(s) or ureter(s) in a subject, the method comprising recording conductivity changes occurring in the ureters, bladder and/or kidneys which indicate changes in volume in the ureters, bladder and/or kidney wherein conductivity changes are detected by bioelectrical impedance or electrical impedance tomography and these volumes being compared to control values to indicate the presence or absence of VUR in the test subject, wherein metrics including maximum conductivity change and max-to-mean ratio are extracted from images.

5. A method for detecting urine flowing from the bladder to the kidney(s) or ureter(s) in a subject, the method comprising recording conductivity changes occurring in the ureters, bladder and/or kidneys which indicate changes in volume in the ureters, bladder and/or kidney wherein conductivity changes are detected by bioelectrical impedance or electrical impedance tomography and these volumes being compared to control values to indicate the presence or absence of VUR in the test subject, wherein the volume of urine travelling to the kidneys is inferred from the residual volume of urine left in the bladder following urination.

6. A device for detecting urine flowing from the bladder to the kidney(s) or ureter(s) in a subject, the device comprising an impedance measurement module and a processor, the device being configured to carry out the method of claim 1.

7. The device of claim 6, further comprising a wetness indicator, and/or a humidity or temperature sensor.

8. The device of claim 6, further comprising an oscillator adapted to indicate if excessive movement of the patient has resulted in noise that would impact the accuracy of the results.

9. A device for detecting urine flowing from the bladder to the kidney(s) or ureter(s) in a subject, the device comprising an impedance measurement module and a processor, the device being configured to carry out the method of claim 2.

10. A device for detecting urine flowing from the bladder to the kidney(s) or ureter(s) in a subject, the device comprising an impedance measurement module and a processor, the device being configured to carry out the method of claim 3.

11. A device for detecting urine flowing from the bladder to the kidney(s) or ureter(s) in a subject, the device comprising an impedance measurement module and a processor, the device being configured to carry out the method of claim 4.

12. A device for detecting urine flowing from the bladder to the kidney(s) or ureter(s) in a subject, the device comprising an impedance measurement module and a processor, the device being configured to carry out the method of claim 5.

* * * * *